US009017675B2

(12) United States Patent
Liu et al.

(10) Patent No.: US 9,017,675 B2
(45) Date of Patent: Apr. 28, 2015

(54) HUMANIZED AND CHIMERIC MONOCLONAL ANTIBODIES TO CD47

(71) Applicant: The Board of Trustees of the Leland Stanford Junior University, Palo Alto, CA (US)

(72) Inventors: Jie Liu, Palo Alto, CA (US); Irving L. Weissman, Stanford, CA (US); Ravindra Majeti, Standford, CA (US)

(73) Assignee: The Board of Trustees of the Leland Sanford Junior University, Palo Alto, CA (US)

( * ) Notice: Subject to any disclaimer, the term of this patent is extended or adjusted under 35 U.S.C. 154(b) by 184 days.

(21) Appl. No.: 13/675,274

(22) Filed: Nov. 13, 2012

(65) Prior Publication Data
US 2013/0142786 A1  Jun. 6, 2013

Related U.S. Application Data

(63) Continuation-in-part of application No. PCT/US2011/036535, filed on May 13, 2011.

(60) Provisional application No. 61/395,652, filed on May 14, 2010.

(51) Int. Cl.
*C07K 16/00* (2006.01)
*C07K 16/46* (2006.01)
*C07K 16/24* (2006.01)
*C07K 16/28* (2006.01)
*G01N 33/68* (2006.01)

(52) U.S. Cl.
CPC ......... *C07K 16/2896* (2013.01); *C07K 2317/24* (2013.01); *C07K 2317/70* (2013.01); *G01N 33/6872* (2013.01); *C07K 16/2803* (2013.01)

(58) Field of Classification Search
None
See application file for complete search history.

(56) References Cited

U.S. PATENT DOCUMENTS

| 4,867,973 | A |   | 9/1989  | Goers et al. |
|-----------|---|---|---------|--------------|
| 5,057,604 | A | * | 10/1991 | Brown ................... 530/388.22 |
| 6,465,247 | B1|   | 10/2002 | Weissman et al. |
| 6,491,917 | B1|   | 12/2002 | Thomas et al. |
| 6,733,743 | B2|   | 5/2004  | Jordan et al. |
| 2003/0108546 | A1 | | 6/2003 | Fukushima et al. |
| 2005/0058645 | A1 | | 3/2005 | Dunlop et al. |
| 2005/0118164 | A1 | | 6/2005 | Herman et al. |
| 2005/0142539 | A1 | | 6/2005 | Herman et al. |
| 2006/0239910 | A1 | | 10/2006 | Nicolaides et al. |
| 2007/0111238 | A1 | | 5/2007 | Jamieson et al. |
| 2007/0113297 | A1 | | 5/2007 | Yang et al. |
| 2007/0287163 | A1 | | 12/2007 | Geuijen et al. |
| 2008/0107654 | A1 | | 5/2008 | Kikuchi et al. |
| 2008/0131431 | A1 | | 6/2008 | Smith et al. |
| 2008/0187950 | A1 | | 8/2008 | Weissman et al. |
| 2010/0255575 | A1 | | 10/2010 | Weissman et al. |
| 2011/0135641 | A1 | * | 6/2011 | Isenberg et al. ............ 424/133.1 |

FOREIGN PATENT DOCUMENTS

| EP | 1693385    | 8/2006 |
|----|------------|--------|
| WO | 99/10478   | 3/1999 |
| WO | 2005044857 | 5/2005 |
| WO | 2008035894 | 3/2008 |

OTHER PUBLICATIONS

Beiboer et al., Guided selection of a pan carcinoma specific antibody reveals similar binding characteristics yet structural divergence between the original murine antibody and its human equivalent. J. Mol. Biol. 296: 833-849 (2000).*
Klimka et al.,Human anti-CD30 recombinant antibodies by guided phage antibody selection using cell panning. British Journal of Cancer (2000) 83:252-260.*
Akashi; et al. "A clonogenic common myeloid progenitor that gives rise to all myeloid lineages", Nature (Mar. 2000), 404(6774):193-197.
Baxter; et al. "Acquired mutation of the tyrosine kinase JAK2 in human myeloproliferative disorders", The Lancet (Mar. 2005), 365(9464):1054-1061.
Brooke; et al. "Human Lymphocytes Interact Directly with CD47 Through a Novel Member of the Signal Regulatory Protein (SIRP) Family", The Journal of Immunology (Aug. 2004), 173(4):2562-2570.
Brown; et al. "Integrin-associated protein: a 50-kD plasma membrane antigen physically and functionally associated with integrins", J Cell Biol (Dec. 1990), 111(6 Pt 1):2785-2794.
Clarke; et al. "Cancer stem cells—perspectives on current status and future directions: AACR Workshop on cancer stem cells", Cancer Research (Oct. 2006), 66(19):9339-9344.
Demeure; et al. "CD47 Engagement inhibits cytokine production and maturation of human dendritic cells", The Journal of Immunology (Feb. 2000), 164(4):2193-2199.
Eichler; et al. "CD97 isoform expression in leukocytes", J of Leukocyte Biology (Oct. 2000), 68(4):561-567.
Fey; et al. "ESMO Minimum Clinical Recommendations for diagnosis, treatment and follow-up of acute myeloblastic leukaemia (AML) in adult patients", Ann Oncol (Aug. 2003), 14(8):1161-1162.
Fuchs; et al. "Cutting Edge: CD96 (Tactile) Promotes NK Cell-Target Cell Adhesion by Interacting with the Poliovirus Receptor (CD155)", J Immunology (Apr. 2004), 172(7):3994-3998.

(Continued)

*Primary Examiner* — Maher Haddad
(74) *Attorney, Agent, or Firm* — Bozicevic, Field & Francis LLP; Pamela J. Sherwood

(57) ABSTRACT

Humanized or chimeric anti-CD47 monoclonal antibodies are provided. The antibodies bind to and neutralize human CD47, and find use in various therapeutic methods. Preferred are non-activating antibodies. Embodiments of the invention include isolated antibodies and derivatives and fragments thereof, pharmaceutical formulations comprising one or more of the humanized or chimeric anti-CD47 monoclonal antibodies; and cell lines that produce these monoclonal antibodies. Also provided are amino acid sequences of the antibodies.

8 Claims, 14 Drawing Sheets

(56) References Cited

OTHER PUBLICATIONS

Gleason; et al. "Tim-3 is an inducible human natural killer cell receptor that enhances interferon gamma production in response to galectin-9", Blood (Feb. 2012), 119(13):3064-3072.
Hebeis; et al. "Vav proteins are required for B-lymphocyte responses to LPS", Blood (Jul. 2005), 106(2):635-640.
Hosen; et al. "CD96 is a leukemic stem cell-specific marker in human acute myeloid leukemia", PNAS (Jun. 2007), 104(26):11008-11013.
Imayoshi; et al. "Expression of CD180, a toll-like receptor homologue, is up-regulated in children with Kawasaki disease", J Mol Med (Feb. 2006), 84(2):168-174.
Imbert; et al. "CD99 expressed on human mobilized peripheral blood CD34+ cells is involved in transendothelial migration", Blood (Oct. 2006), 108(8)2578-2586.
James; et al. "A unique clonal JAK2 mutation leading to constitutive signaling causes polycythaemia vera", Nature (Jun.-Jul. 2005), 434:1144-1148.
Jamieson; et al. "Chronic versus acute myelogenous leukemia: A question of self-renewal", Cancer Cell (Dec. 2004), 6(6):531-533.
Jamieson; et al. "Granulocyte-macrophage progenitors as candidate leukemic stem cells in blast-crisis CML", New England Journal of Medicine (Aug. 2004), 351(7):657-67.
Jamieson; et al. "Increased expression of CD47 is a constant marker in mouse and human myeloid leukemias", Blood (Jan. 2005), 106:911A.
Jan; et al. "Prospective separation of normal and leukemic stem cells based on differential expression of TIM3, a human acute myeloid leukemia stem cell marker", PNAS (Mar. 2011), 108(12):5009-5014.
Jin; et al. "Targeting of CD44 eradicates human acute myeloid leukemic stem cells", Nature Medicine (Oct. 2006), 12 (10):1167-1174.
Kikushige; et al. "TIM-3 Is a Promising Target to Selectively Kill Acute Myeloid Leukemia Stem Cells", Cell Stem Cell (Dec. 2010), 7(6):708-717.
Kralovics; et al. "A gain-of-function mutation of JAK2 in myeloproliferative disorders", New Engl J Med (Apr. 2005), 352(17):1779-1790.
Levine; et al. "Activating mutation in the tyrosine kinase JAK2 in polycythemia vera,essential thrombocythemia, and myeloid metaplasia with myelofibrosis", Cancer Cell (Apr. 2005), 7(4):387-397.
Lindberg; et al. "Molecular cloning of integrin-associated protein: an immunoglobulin family member with multiple membrane-spanning domains implicated in alpha v beta 3-dependent ligand binding", J Cell Biol (Oct. 1993),123 (2):485-496.
Liu; et al. "Signal Regulatory Protein (SIRalpha), a Cellular Ligand for CD47, Regulates Neutrophil Transmigration", Journal of Biological Chemistry (Mar. 2002), 227(12):10028-10036.
Majeti; et al. "CD47 is an adverse prognostic factor and therapeutic antibody target on human acute myeloid leukemia stem cells", Developmental Cell (Jul. 2009), 138(2):286-299.
Majeti; et al. "CD47 Is an Independent Prognostic Factor and Therapuetic Antibody Target on Human Acute Myeloid Leukemia Stem Cells", Blood (Nov. 2008), 112(11):abstract only.
Manna; et al. "CD47 mediates killing of breast tumor cells via Gi-dependent inhibition of protein kinase A", Cancer Research (Feb. 2004), 64(3):1026-1036.
Passegue; et al. "JunB deficiency leads to a myeloproliferative disorder arising from hematopoietic stem cells", Cell (Oct. 2004), 119(3):431-443.
Rebres; et al. "Novel CD47-dependent intercellular adhesion modulates cell migration", J Cell Physiol (Nov. 2005), 205(2):182-193.
Rosales; et al. "Expression of the 50-kDa integrin-associated protein on myeloid cells and erythrocytes", (Oct. 1992), 149(8):2759-2764.
Subramanian; et al. "Species- and cell type-specific interactions between CD47 and human SIRPalpha", (Mar. 2006), 107(6):2548-2556.
Sutherland; et al. "Characterization of a hierarchy in human acute myeloid leukemia progenitor cells", Blood (Jun. 1996), 87(11):4754-4761.
Willingham; et al. "The CD47-signal regulatory protein alpha (SIRa) interaction is a therapeutic target for human solid tumors", PNAS (Apr. 2012), 109(17):6662-6667.
Gresham, H.D., et al. A Novel Member of the Integrin Receptor Family Mediates Arg-Gly-Asp- stimulated Neutrophil Phagocytosis, The Journal of Cell Biology, vol. 108, No. 5, May 1, 1989, pp. 1935-1943, XP055163826, ISSN: 0021-9525, DOI: 10.1083/jcb.108.5.1935.
Brown E, et al., Integrin-associated Protein: A 50 kD Plasma Membrane Antigen Physically and Functionally Associated with Integrins, The Journal of Cell Biology: JCB, The Rockefeller University Press, US, vol. 111, No. 6, Part 01, Dec. 1, 1990, pp. 2785-2794, XP002105095, ISSN: 0021-9525, DOI: 10.1083/JCB.111.6.2785.
Lindberg, F.P., et al., Molecular Cloning of Integrin-associated Protein: An Immunoglobulin Family Member with Multiple Membrane-spanning Domains Implicated Inalphavbeta3-Dependent Ligand Binding, The Journal of Cell Biology: JCB, The Rockefeller University Press, US, vol. 123, No. 2, Oct. 1, 1993, pp. 485-496, XP002929109, ISSN: 0021-9525, DOI: 10.1083/JCB.123.2.485.
Mejeti, Ravindra, et al. CD47 Is an Adverse Prognostic Factor and Therapeutic Antibody Target on Human Acute Myeloid Leukemia Stem Cells, Developmental Cell, Cell Press, Cambridge, MA, US, vol. 138, No. 2, Jul. 23, 2009, pp. 286-299, ZP002632714, ISSN: 1097-4172, DOI: 10.1016/J.Cell.2009.05.045.
Subramanian, S. et al., The 'metabolon', CD47, and the 'phagocytic synapse': molecular co-localization and species divergence, Transfusion Clinique et biologique vol. 13 No. 1-2, Mar. 1, 2006, pp. 31-38.
Selli C., et al., Asynchronous Bilateral Non-Hodgkin's Lymphoma of the Testis: Report of Three Cases, Urology, Dec. 1, 1994, pp. 930-932, vol. 44, No. 6, Belle Mead, NJ, US.
Petterson, Rolf D., CD47 Signals T Cell Death, The Journal of Immunology, the American Association of Immunologist, Jan. 1, 1999, pp. 7031-7040, vol. 162, US.
Subramanian, S. et al., Membrane mobility and clustering of Integrin Associated Protein (IAP, CD47)—Major differences between mouse and man and implications for signaling, Blood Cells, Molecules and Diseases, May 6, 2006, pp. 364-372, vol. 36, No. 3, Lajolla, US.

\* cited by examiner

Figure 1A

EVQLVESGGDLVKPGGSLKLSCAASGFTF

<u>CDR1</u>　　　　　　　　　<u>CDR2</u>
SGYGMSWVRQTPDKRLEWVATITSGGTY

TYYPDSVKGRFTISRDNAKNTLYLQIDSLK

<u>CDR3</u>
SEDTAIYFCARSLAGNAMDYWGQGTSVTVSS

Figure 1B

<u>CDR1</u>
DIVMTQSPATLSVTPGDRVSLSCRASQTISD

<u>CDR2</u>
YLHWYQQKSHESPRLLIKFASQSISGIPSRF

<u>CDR3</u>
SGSGSGSDFTLSINSVEPEDVGVYYCQNG

HGFPRTFGGGTKLEIK

Figure 4A

GAGGTGCAGCTGGTGGAGTCTGGGGGAGGCTTGGTCCAGCCTGGGGGGTCCCTGAGACTC
TCCTGTGCAGCCTCTGGATTCACCTTTAGTGGCTATGGCATGAGCTGGGTCCGCCAGGCT
CCAGGGAAGGGGCTGGAGTGGGTGGCCACCATAACTAGTGGTGGAACTTACACCTACTAT
CCAGACTCTGTGAAGGGCCGATTCACCATCTCCAGAGACAACGCCAAGAACTCACTGTAT
CTGCAAATGAACAGCCTGAGAGCCGAGGACACGGCTGTGTATTACTGTGCGAGATCCCTC
GCGGGAAATGCTATGGACTACTGGGGCCAAGGAACCCTGGTCACCGTCTCCTCA

Figure 4B

GAAATTGTGTTGACACAGTCTCCAGCCACCCTGTCTTTGTCTCCAGGGGAAAGAGCCACC
CTCTCCTGCAGGGCCAGTCAGACTATTAGCGACTACTTACACTGGTACCAACAGAAACCT
GGCCAGGCTCCCAGGCTCCTCATCAAATTTGCATCCCAATCCATTTCTGGCATCCCAGCC
AGGTTCAGTGGCAGTGGGTCTGGGACAGACTTCACTCTCACCATCAGCAGCCTAGAGCCT
GAAGATTTTGCAGTTTATTACTGTCAGAATGGTCACGGCTTTCCTCGGACGTTCGGCCAA
GGGACCAAGGTGGAAATCAAA

Figure 8A Alignments of human V-J combinations

```
>> VK3-11_JK1 or 3-11-1 for short
initn: 591 init1: 591 opt: 591  Z-score: 694.8  bits: 133.6 E(): 3.2e-34
Smith-Waterman score: 591; 85.047% identity (85.047% ungapped) in 107 aa overlap (1-107:1-107)

10        20        30        40        50        60
HuB6     EIVLTQSPATLSLSPGERATLSCRASQSVTSDYLAWYQQKPGQAPRLLIKYASQSISGIPA
         ::::::::::::::::::::::::::::  ::  ::::::::::::::: :::::::::::
3-11-1   EIVLTQSPATLSLSPGERATLSCRASQSVSSYLAWYQQKPGQAPRLLIYDASNRATGIPA
               10        20        30        40        50        60

70        80        90        100
HuB6     RFSGSGSGTDFTLTISSLEPEDFAVYYCQQHGFPRTFGQGTKVEIK
         ::::::::::::::::::::::::::::   :: : ::::::::::
3-11-1   RFSGSGSGTDFTLTISSLEPEDFAVYYCQQRSNWPLTFGQGTKVEIK
               70        80        90        100
```

Figure 8B

```
>>VH3-07_JH4 or 3-07-4 for short
initn: 639 init1: 580 opt: 580  Z-score: 650.1  bits: 125.5 E(): 1e-31
Smith-Waterman score: 625; 83.898% identity (90.826% ungapped) in 118 aa overlap (1-118:1-109)

10        20        30        40        50        60
HuB6     EVQLVESGGGLVQPGGSLRLSCAASGFTFSGYGMSWVRQAPGKGLEWVAIIYSGGTYTYY
         :::::::::::::::::::::::::::::: ::::::::::::::::::: ::::: :: 
3-07-4   EVQLVESGGGLVQPGGSLRLSCAASGFTFSSYWMSWVRQAPGKGLEWVANIKQDGSEKYY
               10        20        30        40        50        60

70        80        90        100       110
HuB6     ADSVKGRFTISRDNAKNSLYLQMNSLRAEDTAVYYCARSLASWAMDYWGQGTLVTVSS
         ::::::::::::::::::::::::::::::::::::::::                ::::::::::
3-07-4   VDSVKGRFTISRDNAKNSLYLQMNSLRAEDTAVYYCAR----------WGQGTLVTVSS
               70        80        90        100
```

Figure 8C

| Segment | LC Differences | HC Differences |
|---|---|---|
| FRM1 | 0 | 0 |
| CDR1 | 4 | 2 |
| FRM2 | 1 | 0 |
| CDR2 | 5 | 8 |
| FRM3 | 0 | 0 |
| CDR3 | 6 | n/a |
| FRM4 | 0 | 0 |

Figure 9A

CDR1

QVQLQQPGAELVKPGASVMMSCKASGYTFTNYNMHWVKQTPGQG

CDR2

LEWIGTIYPGNDDTSYNQKFKDKATLTADKSSSAAYMQLSSLTSEDSA

CDR3

VYYCARGGYRAMDYWGQGTSVTVSS

Figure 9B

CDR1

DVLMTQTPLSLPVSLGDQASISCRSSQSIVYSNGNTYLGWYLQK

CDR2

PGQSPKLLIYKVSNRFSGVPDRFSGSGSGTDFTLKISRVEAEDLG

CDR3

VYHCFQGSHVPYTFGGGTKVEIK

Figure 10A

CDR1

EVQLQQSGPELVKPGASVKMSCKASGYTFTTYVVHWVKQTPGQGL

CDR2

EWIGYINPYNDGTKYNEKFKGKATLTSDKSSSTAYMEFSSLTSEDSA

CDR3

VYYCVRGYYRYGYTMDYWGQGTSVTVSS

Figure 10B

CDR1

DIVMTQSPATLSVTPGDRVSLCRASQNFSDYLHWYQQK

CDR2

SHESPRLLIKYVSHSISGIPSRFSGSGSGSDFTLSINSVEPE

CDR3

DVGVYYCQNGHSFPPTFGGGTKLEIK

Figure 12A

```
hu5F9-vh1     QVQLVQSGAEVKKPGASVKVSCKASGYTFTNYNMHWVRQAPGQG
hu5F9-vh2     QVQLVQSGAEVKKPGASVKVSCKASGYTFTNYNMHWVRQAPGQR
hu5F9-vh3     QVQLVQSGAEVKKPGASVKVSCKASGYTFTNYNMHWVRQAPGQR
IGHV1-03-01   QVQLVQSGAEVKKPGASVKVSCKASGYTFTSYAMHWVRQAPGQR
IGHV1-46-03   QVQLVQSGAEVKKPGASVKVSCKASGYTFTSYYMHWVRQAPGQG
mouse 5F9VH   QVQLQQPGAELVKPGASVMMSCKASGYTFTNYNMHWVKQTPGQG hu5F9-vh1     LEWIGTIYPGNDDTSYNQKFKDKATLTADKSTSTAYMELSSLRS
hu5F9-vh2     LEWMGTIYPGNDDTSYNQKFKDRVTITADTSASTAYMELSSLRS
hu5F9-vh3     LEWIGTIYPGNDDTSYNQKFKDRATLTADKSASTAYMELSSLRS
IGHV1-03-01   LEWMGWINAGNGNTKYSQKFQGRVTITRDTSASTAYMELSSLRS
IGHV1-46-03   LEWMGIINPSGGSTSYAQKFQGRVTMTRDTSTSTVYMELSSLRS
mouse 5F9VH   LEWIGTIYPGNDDTSYNQKFKDKATLTADKSSSAAYMQLSSLTS hu5F9-vh1     EDTAVYYCARGGYRAMDYWGQGTLVTVSS
hu5F9-vh2     EDTAVYYCARGGYRAMDYWGQGTLVTVSS
hu5F9-vh3     EDTAVYYCARGGYRAMDYWGQGTLVTVSS
IGHV1-03-01   EDTAVYYCAR
IGHV1-46-03   EDTAVYYCAR
mouse 5F9VH   EDSAVYYCARGGYRAMDYWGQGTSVTVSS
```

Figure 12B

```
hu5F9-vl1     DVVMTQSPLSLPVTPGEPASISCRSSQSIVYSNGNTYLGWYLQK
hu5F9-vl2     DIVMTQSPLSLPVTPGEPASISCRSSQSIVYSNGNTYLGWYLQK
hu5F9-vl3     DVVMTQSPLSLPVTPGEPASISCRSSQSIVYSNGNTYLGWYLQK
IGKV2-28-01   DIVMTQSPLSLPVTPGEPASISCRSSQSLLHSNGYNYLDWYLQK
mouse 5F9 VL  DVLMTQTPLSLPVSLGDQASISCRSSQSIVYSNGNTYLGWYLQK hu5F9-vl1     PGQSPKLLIYKVSNRFSGVPDRFSGSGSGTDFTLKISRVEAEDV
hu5F9-vl2     PGQSPQLLIYKVSNRFSGVPDRFSGSGSGTDFTLKISRVEAEDV
hu5F9-vl3     PGQSPQLLIYKVSNRFSGVPDRFSGSGSGTDFTLKISRVEAEDV
IGKV2-28-01   PGQSPQLLIYLGSNRASGVPDRFSGSGSGTDFTLKISRVEAEDV
mouse 5F9 VL  PGQSPKLLIYKVSNRFSGVPDRFSGSGSGTDFTLKISRVEAEDL hu5F9-vl1     GVYHCFQGSHVPYTFGGGTKVEIK
hu5F9-vl2     GVYYCFQGSHVPYTFGQGTKLEIK
hu5F9-vl3     GVYHCFQGSHVPYTFGQGTKLEIK
IGKV2-28-01   GVYYCMQALQTP
mouse 5F9 VL  GVYHCFQGSHVPYTFGGGTKVEIK
```

HUMANIZED AND CHIMERIC MONOCLONAL ANTIBODIES TO CD47

BACKGROUND OF THE INVENTION

Macrophages clear pathogens and damaged or aged cells from the blood stream via phagocytosis. Cell-surface CD47 interacts with its receptor on macrophages, SIRPα, to inhibit phagocytosis of normal, healthy cells. CD47 is a broadly expressed transmembrane glycoprotein with a single Ig-like domain and five membrane spanning regions, which functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including hematopoietic stem cells.

SIRPα inhibits the phagocytosis of host cells by macrophages, where the ligation of SIRPα on macrophages by CD47 expressed on the host target cell generates an inhibitory signal mediated by SHP-1 that negatively regulates phagocytosis. SIRPα acts to detect signals provided by "self," to negatively control innate immune effector function against these cells.

In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

CD47 is also constitutively upregulated on a number of cancers, including myeloid leukemias. Overexpression of CD47 on a myeloid leukemia line increases its pathogenicity by allowing it to evade phagocytosis. We conclude that CD47 upregulation is an important mechanism that provides protection to normal HSCs during inflammation-mediated mobilization, and that leukemic progenitors co-opt this ability in order to evade macrophage killing.

The present invention provides anti-CD47 antibodies having low immunogenicity in humans.

SUMMARY OF THE INVENTION

Compositions and methods are provided relating to humanized or chimeric anti-CD47 monoclonal antibodies. The antibodies of the invention bind to and neutralize human CD47, and find use in various therapeutic methods. Preferred are non-activating antibodies. Embodiments of the invention include isolated antibodies and derivatives and fragments thereof, pharmaceutical formulations comprising one or more of the humanized or chimeric anti-CD47 monoclonal antibodies; and cell lines that produce these monoclonal antibodies. Also provided are amino acid sequences of the antibodies.

Antibodies of interest include the provided humanized or chimeric antibodies, and variants thereof. The monoclonal antibodies of the invention find particular utility as reagents for the diagnosis and immunotherapy of disease associated with CD47 in humans, particularly in cancer therapy. An advantage of the monoclonal antibodies of the invention derives from the humanization process. Thus, in vivo use of the monoclonal antibodies of the invention for immunotherapy greatly reduces the problems of significant host immune response to the antibodies.

Various forms of the antibodies are contemplated herein. For example, the anti-CD47 antibody may be a full length chimeric or humanized antibody, e.g. having a human immunoglobulin constant region of any isotype, e.g. IgG1, IgG2a, IgG2b, IgG3, IgG4, IgA, etc. or an antibody fragment, e.g. a $F(ab')_2$ fragment, and F(ab) fragment, etc. Fragments comprising CDR regions are also of interest, e.g. for imaging purposes. Furthermore, the antibody may be labeled with a detectable label, immobilized on a solid phase and/or conjugated with a heterologous compound. The antibody may also be provided as a bi-specific or multispecific antibody reactive with a second antigen, particularly including cancer antigens.

Diagnostic and therapeutic uses for the antibody are contemplated, particularly relating to the detection and elimination of undesirable cells expressing CD47. In one diagnostic application, the invention provides a method for determining the presence of CD47 expressing cancer cells, comprising exposing a patient sample suspected of containing CD47 expressing cancer cells to the anti-CD47 antibody and determining binding of the antibody to the sample. For this use, the invention provides a kit comprising the antibody and instructions for using the antibody.

The antibodies of the invention are particularly efficacious in the treatment of disease, e.g. increasing the phagocytosis of CD47 expressing cells. Treatment may be systemic or localized, e.g. delivery by intratumoral injection, etc.

Embodiments of the invention include isolated antibodies and derivatives and fragments thereof that comprise at least one, usually at least 3 CDR sequences from a set, as provided herein, usually in combination with framework sequences from a human variable region or as an isolated CDR peptide. In some embodiments an antibody comprises at least one light chain comprising a set of 3 light chain CDR sequences provided herein situated in a variable region framework, which may be, without limitation, a human or mouse variable region framework, and at least one heavy chain comprising the set of 3 heavy chain CDR sequence provided herein situated in a variable region framework, which may be, without limitation, a human or mouse variable region framework.

In other embodiments, the antibody comprises an amino acid sequence variant of one or more of the CDRs of the provided antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally having a binding affinity for human CD47 of at least about $10^{-8}$ M and will bind to the same epitope as an antibody having the amino acid sequence of those set forth herein. For example, the light chain CDR3 may be modified to mutate the de-amidation site. Various forms of the antibodies are contemplated herein. For example, the antibody may be a full length antibody, e.g. having a human immunoglobulin constant region of any isotype, e.g. IgG1, IgG2a, IgG2b, IgG3, IgG4, IgA, etc. or an antibody fragment, e.g. a $F(ab')_2$ fragment, and F(ab) fragment, etc. Furthermore, the antibody may be labeled with a detectable label, immobilized on a solid phase and/or conjugated with a heterologous compound.

The invention further provides: isolated nucleic acid encoding the antibodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more of the human anti-CD47 antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

FIG. 1. Amino acid sequences of B6H12 heavy chain variable region (A)(SEQ ID NO: 1) and light chain variable region (B)(SEQ ID NO. 2). Complementarity determining regions(CDR) are as indicated.

FIG. 4. Nucleotide sequences for humanized B6H12 heavy chain variable region (A)(SEQ ID NO: 9) and light chain variable region (B) (SEQ ID NO: 10).

FIG. 8. Amino acid alignment between humanized B6H12 VL and human VK3-11 and JK1 (A) SEQ ID NOs: 12 and 34), and humanized B6H12 VH and human VH3-7 and JH4 (B) (SEQ ID NO: 11 and 35. Number of different amino acids of humanized B6H12 and human germline sequences in the framework and CDR regions of VH and VL are summarized in the table (C).

FIG. 9. Amino acid sequences of 5F9 heavy chain variable region (A) (SEQ ID NO: 18) and light chain variable region (B) (SEQ ID No: 19). Complementarity determining regions (CDR) are as indicated.

FIG. 10. Amino acid sequences of 8B6 heavy chain variable region (A) (SEQ ID NO:26) and light chain variable region (B) (SEQ ID NO:27). Complementarity determining regions (CDR) are as indicated.

FIG. 12. Amino-acid sequence alignments of different versions of humanized 5F9 heavy chain variable regions (A) (from the tiop bottom SEQ ID NOs: 36-40 and 18) and light chain variable regions (B) (from top to bottom SEQ ID NOs: 41-44 and 19)with germline sequences. CDR regions are underlined.

DETAILED DESCRIPTION OF THE INVENTION

Figure 2:
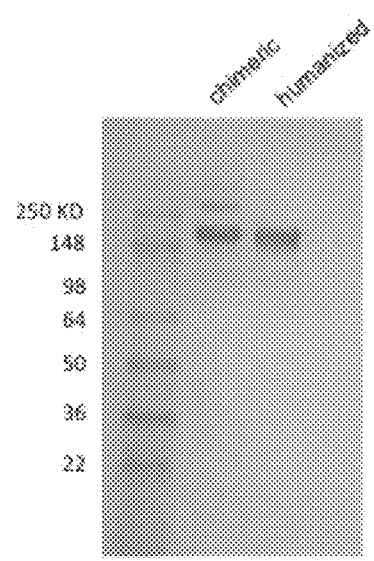
FIG. 2. SDS-PAGE analysis of purified B6H12 proteins. Purified chimeric and humanized B6H12 were analyzed by SDS-PAGE under non-reducing conditions. Molecular mass standards are indicated on the left.

The present invention relates to humanized monoclonal antibodies which are specific for CD47. Also disclosed is a nucleic acid, and amino acid sequence of such antibodies. The antibodies find use in therapeutic and diagnostic methods associated with CD47.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Variable region sequences of interest include the provided humanized variable region sequences for anti-CD47 antibodies: B6H12: SEQ ID NO:11 (heavy chain), SEQ ID NO:12 (light chain); 5F9: SEQ ID NO:36 or 37 or 38 (heavy chain); SEQ ID NO:39 or 40 or 41 (light chain); 8B6: SEQ ID NO:35 (heavy chain), SEQ ID NO:36 (light chain); or C3: SEQ ID NO:53 (heavy) and SEQ ID NO:58 (light chain).

The CDR sequence sets of exemplary anti-CD47 heavy and light chains combinations are set forth in the sequence listing, including B6H12: SEQ ID NO:3-8; 5F9: SEQ ID NO:20-25; 8B6: SEQ ID NO:28-33; and C3: SEQ ID NO:61-63 heavy and SEQ ID NO:64-66 light. In some embodiments the CDR sequences for a particularly heavy and light chain combination as set forth in B6H12, 5F9, 8B6 or C3 will be maintained in a combination, i.e. a humanized antibody will comprise both B6H12 heavy chain CDR sequences and B6H12 heavy chain CDR sequences; or both 5F9 heavy chain CDR sequences and 5F9 heavy chain CDR sequences, or 8B6 heavy chain CDR sequences and 8B6 heavy chain CDR sequences, or both C3 heavy chain CDR sequences and C3 light chain CDR sequences.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-CD47 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-CD47 antibody fused to an "epitope tag". The epitope tag polypeptide has enough residues to provide an epitope against which an antibody can be made, yet is short enough such that it does not interfere with activity of the CD47 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)).

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Polypeptides

In one aspect, the present invention is directed to humanized or chimeric monoclonal antibodies that are specifically reactive with and neutralize CD47, and cell lines that produce such antibodies. Variable regions of exemplary antibodies are provided. Antibodies of interest include these provided combinations, as well as fusions of the variable regions to appropriate constant regions or fragments of constant regions, e.g. to generate F(ab)' antibodies. Variable regions of interest include at least one CDR sequence of the provided anti-CD47 antibody, where a CDR may be 3, 4, 5, 6, 7, 8, 9, 10, 11, 12 or more amino acids. Alternatively, antibodies of interest include a variable region as set forth in the provided antibodies, or pairs of variable regions sequences as set forth herein.

In some embodiments a polypeptide of interest has a contiguous sequence of at least about 10 amino acids, at least about 15 amino acids, at least about 20 amino acids, at least about 25 amino acids, at least about 30 amino acids, up to the complete provided variable region. Polypeptides of interest also include variable regions sequences that differ by up to one, up to two, up to 3, up to 4, up to 5, up to 6 or more amino acids as compared to the amino acids sequence set forth herein. In other embodiments a polypeptide of interest is at least about 80%, at least about 85%, at least about 90%, at least about 95%, at least about 99% identical to the amino acid sequence set forth herein.

In addition to Fabs, smaller antibody fragments and epitope-binding peptides having binding specificity for at least one epitope of CD47 are also contemplated by the present invention and can also be used in the methods of the invention. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escherichia coli*," Nature 341: 644-646, disclose a method for screening to obtain an antibody heavy chain variable region (H single domain antibody) with sufficient affinity for its target epitope to bind thereto in isolate form.

The invention also provides isolated nucleic acids encoding the humanized or chimeric anti-CD47 antibodies, vectors and host cells comprising the nucleic acid, and recombinant techniques for the production of the antibody. Nucleic acids of interest may be at least about 80% identical to the provided nucleic acid sequences, at least about 85%, at least about 90%, at least about 95%, at least about 99%, or identical. In some embodiments a contiguous nucleotide sequence as set forth in any one of the provided coding sequences of at least about 20 nt., at least about 25 nt, at least about 50 nt., at least about 75 nt., at least about 100 nt, and up to the complete provided sequence may be used. Such contiguous sequences may encode a CDR sequence, or may encode a complete variable region. As is known in the art, a variable region sequence may be fused to any appropriate constant region sequence.

For recombinant production of the antibody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The anti-CD47 antibody of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for anti-CD47 antibody production and cultured in conventional nutrient media modified as appropriate for inducing promoters, selecting transformants, or amplifying the genes encoding the desired sequences.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The humanized or chimeric monoclonal antibodies of the invention can be used in the modulation of phagocytosis, including the methods set forth in International Application US2009/000319, herein specifically incorporated by reference in its entirety. For example, antibody compositions may be administered to increase phagocytosis of cancer cells expressing CD47.

The humanized or chimeric monoclonal antibodies of the invention can be used in vitro and in vivo to monitor the course of CD47 disease therapy. Thus, for example, by measuring the increase or decrease in the number of cells expressing CD47, particularly cancer cells expressing CD47, it can be determined whether a particular therapeutic regimen aimed at ameliorating disease is effective.

The monoclonal antibodies of the invention may be used in vitro in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are flow cytometry, e.g. FACS, MACS, immunohistochemistry, competitive and non-competitive immunoassays in either a direct or indirect format; and the like. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of CD47 expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art, which find use as tracers in therapeutic methods, for use in diagnostic methods, and the like. For diagnostic purposes a label may be covalently or non-covalently attached to an antibody of the invention or a fragment thereof, including fragments consisting or comprising of CDR sequences. Examples of the types of labels which can be used in the present invention include enzymes, radioisotopes, fluorescent compounds, colloidal metals, chemiluminescent compounds, and bio-luminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

In some embodiments the antibody or a fragment thereof is attached to a nanoparticle, e.g. for use in imaging. Useful nanoparticles are those known in the art, for example including without limitation, Raman-silica-gold-nanoparticle (R—Si—Au-NP). The R—Si—Au-NPs consist of a Raman organic molecule, with a narrow-band spectral signature, adsorbed onto a gold core. Because the Raman organic molecule can be changed, each nanoparticles can carry its own signature, thereby allowing multiple nanoparticles to be independently detected simultaneously by multiplexing. The entire nanoparticle is encapsulated in a silica shell to hold the Raman organic molecule on the gold nanocore. Optional polyethylene glycol (PEG)-ylation of R—Si—Au-NPs increases their bioavailability and provides functional "handles" for attaching targeting moieties (see Thakor et al (2011) Sci Transl Med. 3(79):79ra33; Jokerst et al. (2011) Small. 7(5):625-33; Gao et al. (2011) Biomaterials. 32(8): 2141-8; each herein specifically incorporated by reference).

For purposes of the invention, CD47 may be detected by the monoclonal antibodies of the invention when present in biological fluids and on tissues, in vivo or in vitro. Any sample containing a detectable amount of CD47 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD47 associated disease.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The anti-CD47 antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-CD47 antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-CD47 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Cloning and Generation of Monoclonal Antibodies Directed Against Human CD47

We describe here the cloning, construction and expression of monoclonal antibodies directed against human CD47. From a mouse hybridoma cell line secreting B6H12, a functional blocking antibody directed against human CD47, total RNA was prepared and converted into cDNA using Ig-specific oligonucleotides. Heavy and light chain encoding cDNA fragments were isolated and sequenced. Chimeric genes were then constructed by linking the murine V region cDNA fragments to human immunoglobulin constant regions. By competitive FACS analysis, chimeric B6H12 inhibited the binding of native mouse B6H12 antibody to CD47, demonstrating that the chimeric and mouse B6H12 antibodies recognize the same epitope of CD47. Furthermore, we designed and constructed a humanized B6H12 antibody by CDR grafting. The humanized B6H12 antibody showed comparable CD47 binding to that of chimeric B6H12. Both chimeric and humanized B6H12 antibodies enable phagocytosis of cancer cells in vitro. We anticipate that the chimeric and humanized antibodies will be less immunogenic than the native mouse antibody when administered to human patients as part of anti-cancer therapy.

We have identified and validated leukemia stem cell-preferential expression of CD47 using antigen specific monoclonal antibodies. CD47 is a widely expressed transmembrane protein; however, we found that CD47 was more highly expressed on AML LSC than their normal counterparts, and that increased CD47 expression predicted worse overall survival in three independent cohorts of adult AML patients. CD47 serves as the ligand for signal regulatory protein alpha (SIRPα), which is expressed on phagocytic cells including macrophages and dendritic cells, that when activated initiates a signal transduction cascade resulting in inhibition of phagocytosis. When we used a blocking monoclonal antibody directed against CD47, it preferentially enabled phagocytosis of AML LSC and inhibited their engraftment in vivo. Furthermore, treatment of human AML LSC-engrafted mice with anti-CD47 antibody depleted AML and targeted AML LSC. These results establish a rationale for anti-CD47 monoclonal antibodies as monotherapy or combination therapy for AML and other cancers.

Here we report the isolation, synthesis, and generation of a human IgG1 chimeric monoclonal antibody-derived from B6H12, and a humanized B6H12 antibody engineered by CDR grafting. We describe the construction of chimeric and humanized immunoglobulin genes composed of the cDNAs encoding the variable regions of heavy and light chains fused to human γ1 and κ constant regions, respectively. Introduction of these genes into mammalian cells resulted in production of functional chimeric and humanized antibodies able to bind human CD47 and cause phagocytosis of target cells.

Materials and Methods

Antibody V cloning and sequencing. The cloning strategy used here involved the initial isolation of RNA from hybridoma cells (Qiagen), and preparation of cDNA. cDNA sequences encoding the heavy and light chain variable regions of the B6H12 monoclonal antibody were obtained using 5' RACE-PCR techniques (Clontech) and were sequenced using standard DNA sequencing techniques.

Construction of B6H12/hIgG1 chimeric antibody. In order to construct the heavy and light chain variable regions of B6H12 in an expression vector, the following primers were used:

```
VH sense primer,
5' CAGACCCGTCGACATGAACTTCGGGCTCAGCTTGATTTTCCTT 3'
(SEQ ID NO: 45)

VH antisense primer,
5' GCCCTTGGTGCTAGCTGAGGAGACGGTGACTGAGGTTCCTTGAC
C 3' (SEQ ID NO: 46)

VL sense primer,
5' CGCCATCACAGATCTATGGTGTCCACTTCTCAGCTCCTTGGACT
T 3' (SEQ ID NO: 47)

VL antisense primer,
5' TGCAGCCACCGTACGTTTGATTTCCAGCTTGGTGCCTCCACCGA
A 3' (SEQ ID NO: 48).
```

PCR was then performed using cloned pfu DNA polymerase (Invitrogen). These PCR products were cut by SalI/NheI for the VH and BglII/BsiwI for the VL and ligated into an expression vector encoding human gamma 1 and kappa constant regions that was digested by SalI/NheI or BglII/BsiwI, respectively. All constructs were sequenced to confirm sequence fidelity.

Molecular Modeling. Humanization of mouse anti-CD47 B6H12 antibody was performed by installing CDR residues from the mouse antibody into human germline framework (FR) sequences. Briefly, mouse B6H12 was humanized by judicious recruitment of corresponding CDR residues and a few FR residues into the human sequences. Differences between mouse B6H12 and the human FR residues were individually modeled to investigate their possible influence on CDR conformation. Humanized VH and VL genes were synthesized by McLab (South San Francisco, Calif.).

Cell transfection and stable cell line establishment. Stable cell lines expressing chimeric or humanized B6H12 were established by transfection of the expression construct into CHOS cells using DMRIEC transfection reagent (Invitrogen) according to the manufacturer's instructions. Three days later, transfected cells were selected under 500 ug/ml G418. Stable clones were isolated by limited dilution in 96-well plates. To screen G418-resistant clones for their ability to secrete antibody, supernatants of the transfected cells were tested by ELISA. Briefly, 96-well plates (Nunc, Roskilde, Denmark) were coated with 1 ug/ml goat anti-human Fc gamma antibody in PBS for 16 h at 4° C. After blocking for 1 h with 0.4% BSA in PBS at room temperature, isolated supernatants were added in ⅓ sequential dilutions, and incubated for 1 h at room temperature. Plates were subsequently washed three times and incubated with HRP-conjugated goat anti-human kappa-specific antibody for 1 h at room temperature. After washing, plates were developed with OPT. The reaction was stopped with 2M $H_2SO_4$, and OD was measured at 520 nM. Positive clones were further expanded and expression was confirmed by ELISA.

Antibody purification and characterization. The culture supernatant was applied to protein G Sepharose columns. The column was washed with phosphate-buffered saline (PBS) pH 8.0, and protein was then eluted with eluting buffer (glycine pH 2.0). The eluted fractions were collected in tubes containing neutralizing buffer (2M Tris-HCl, pH 8.0) to adjust the pH to approximately 7.0. Finally, purified samples were dialyzed against phosphate-buffered saline (PBS). Purity of the eluted antibody fraction was analyzed by sodium dodecyl sulfate polyacrylamide gel electrophoresis (SDS-PAGE) on 10% gels under reducing or non-reducing conditions. Bands were visualized by Coomassie brilliant blue staining.

Binding specificity by ELISA. Microtiter plates were coated with 100 µl purified human CD47-Fc fusion protein at 1.0 µg/ml in PBS, and then blocked with 100 µl of 0.4% BSA in PBS. Dilutions of the B6H12 chimeric or humanized antibody were added to each well and incubated for 1 hour at room temperature. A known murine anti-CD47 antibody was used as a positive control, and human IgG1 was used as an isotype control. The plates were washed with PBS/Tween and then incubated with a goat anti-human kappa-specific secondary reagent conjugated to horseradish peroxidase for 1 hour at room temperature. After washing, the plates were developed with OPT substrate, and analyzed at OD of 520 nm.

Binding specificity by FACS. YB2/0 cells that had been stably transfected with human CD47 were incubated with various amounts of chimeric B6H12, humanized B6H12, or a human IgG1 isotype control antibody on ice for 1 hr. The cells were washed three times with FACS buffer (PBS containing 0.5% BSA and 0.05% $NaN_3$). PE labeled goat anti-human antibody was added as a secondary antibody, and the samples were incubated on ice for another 1 hour. Samples were washed and analyzed using a FACSAria (Becton-Dickinson, San Jose, Calif., USA).

Competitive binding assay by FACS. Binding inhibition of the chimeric B6H12 antibody to human CD47 by the mouse antibody B6H12 or an isotype control antibody was measured using FACS. CD47-transfected YB2/0 cells were harvested and washed twice with FACS buffer (PBS containing 0.5% BSA and 0.05% $NaN_3$). Then chimeric B6H12 was added to the cells at a final concentration of 1 ug/ml with various amounts of mouse B6H12 antibody or an isotype control antibody and incubated for 1 hour on ice. Similarly, binding inhibition of the mouse B6H12 antibody to human CD47 was measured by adding various amounts of the chimeric B6H12 or an isotype control antibody. The samples were washed with FACS buffer, PE labeled goat anti-human or anti-mouse antibody was added, and the samples were incubated on ice for another 1 hour. Samples were washed and analyzed using a FACSAria (Becton-Dickinson, San Jose, Calif., USA).

In vitro phagocytosis assays. HL-60 cells were CFSE-labeled and incubated with mouse bone marrow-derived macrophages in the presence of 10 μg/ml IgG1 isotype control, mouse B6H12, chimeric B6H12, or humanized B6H12 antibody for 2 hr. Cells were then analyzed by fluorescence microscopy to determine the phagocytic index (number of cells ingested per 100 macrophages). Statistical analysis using Student's t-test was performed with GraphPad Prism.

Results

Cloning of Mouse B6H12 Variable Regions.

Using universal antibody primers, clones encoding heavy and light chain variable regions were successfully isolated from an anti-CD47 B6H12 hybridoma. Multiple clones of each V gene product were sequenced to monitor PCR-induced errors. The VH and VL sequences are shown in FIGS. 1A and B, respectively. DNA sequence analysis for products demonstrated that the heavy chain of B6H12 uses a V segment of the Igh-v7183 VH5 family, and that the light chain belongs to the IGKV23 subgroup. The heavy chain variable region comprises CDR1, CDR2, and CDR3 sequences; and the light chain variable region comprises CDR1, CDR2, and CDR3 sequences (FIG. 1).

Production and Characterization of B6H12 Chimeric Antibodies.

To construct the expression vector for chimeric B6H12 antibody, the heavy chain variable region of B6H12 that includes its native signal peptide sequence at the $NH_2$ terminus was fused to the constant region of the human γ1 heavy chain and then cloned into a mammalian expression vector. Similarly, the light chain variable region of B6H12 that includes its native signal peptide sequence at the $NH_2$ terminus was fused to the constant region of human κ light chain and introduced into the vector encoding the B6H12 heavy chain. The resulting single expression vector was then transfected into mammalian cells. Expressed chimeric B6H12 antibody was purified and examined by SDS-PAGE analysis. As expected, one single band with a molecular mass of ~150 kDa was observed under nonreducing conditions (FIG. 2). After reduction with 2-mercaptoethanol, two bands appeared at 50 kDa and 25 kDa, corresponding to heavy and light chains, respectively. These results indicate that chimeric heavy and light chain peptides produced in the transfectant were assembled to form the native IgG molecule.

Figure 3A:
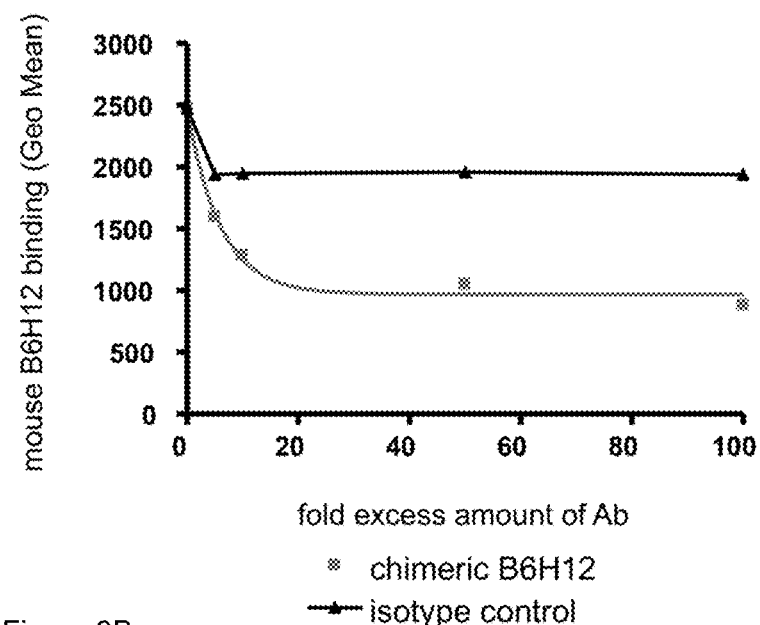
FIG. 3. Competition of chimeric B6H12 antibody against mouse B6H12 antibody for CD47 binding. A. Chimeric B6H12 competed against mouse B6H12 for binding to YB2/0 cells that had been stably transfected with human CD47 (YB2/0-CD47). A human IgG1 antibody was used as an isotype control. B. Mouse B6H12 competed against chimeric B6H12 for binding to human CD47 expressed on transfected YB2/0 cells. A mouse IgG1 was used as an isotype control.
Figure 3B:
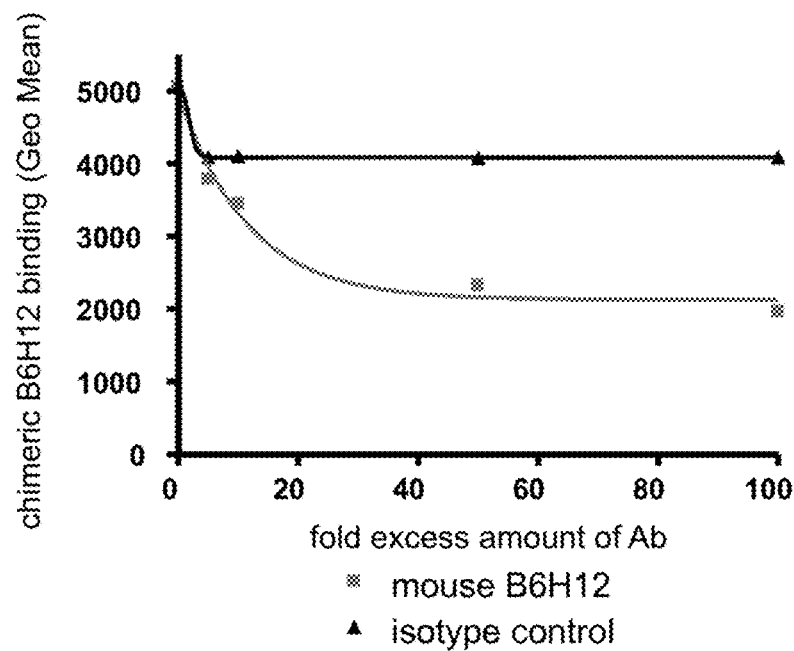

To demonstrate that B6H12 variable regions cloned from the mouse hybridoma retain antigen binding activity similar to the original mouse B6H12 antibody, a competition binding assay between chimeric and mouse B6H12 was conducted by flow cytometry. Human CD47 was stably transfected into YB2/0 cells and the expression of CD47 was confirmed by flow cytometry. As shown in FIG. 3A, chimeric B6H12 competed out mouse B6H12 for CD47 binding in a dose-dependent manner, while a human IgG1 isotype control antibody had no impact on mouse B6H12 binding. Similarly, mouse B6H12 antibody inhibited chimeric B6H12 antibody for CD47 binding (FIG. 3B). This suggests that the chimeric B6H12 antibody recognizes the same epitope of CD47 as the native mouse B6H12 antibody.

Design and Analysis of Humanized B6H12 Antibody.

In order to select human antibody frameworks (FR) to be used as templates for CDR-grafting, mouse B6H12 VL and VH regions were compared with those of human germline sequences. The FRs of the mouse B6H12 VL region were found to have the highest homology with the human VK3 subgroup, suggesting that a member of subgroup III might be the best selection. The FRs of the mouse B6H12 VH region exhibited the highest homology with the human VH-3 subgroup. The FRs from human VH-3-7 and VK3-11 were ultimately selected as the starting point for designing humanized B6H12. Residues in the FRs identical to the mouse sequences were retained and non-identical residues were either retained or substituted based on molecular modeling. The humanized B6H12 was transfected and purified as described above. SDS-PAGE analysis showed one single band with a molecular mass of ~150 kDa under non-reducing conditions (FIG. 2), and two bands appeared at 50 kDa and 25 kDa under reducing conditions. The sequences are shown in FIG. 4.

Figure 5:
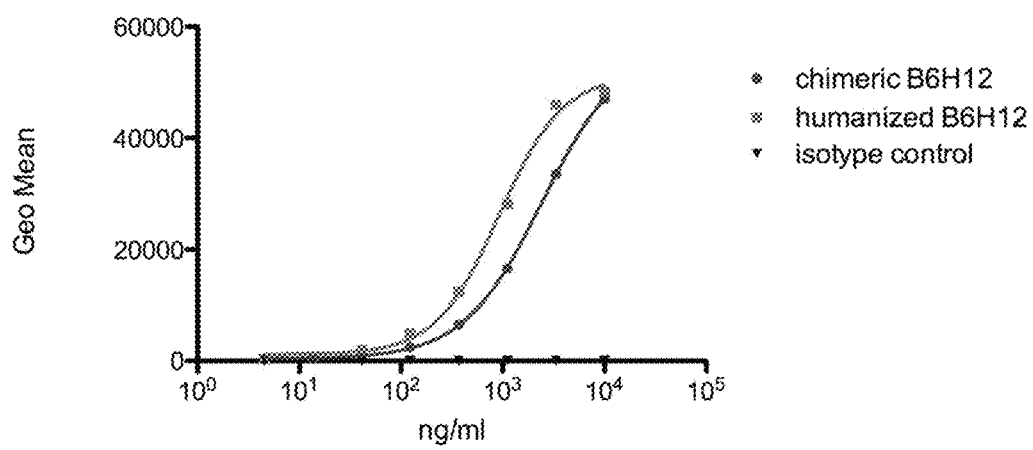
FIG. 5. Comparison of the binding of chimeric and humanized B6H12 antibodies to human CD47 by flow cytometry. YB2/0 cells stably transfected with human CD47 were stained with chimeric B6H12, humanized B6H12, or a human IgG1 isotype control antibody. Bound antibody was detected with PE-labeled secondary antibody.
Figure 6:
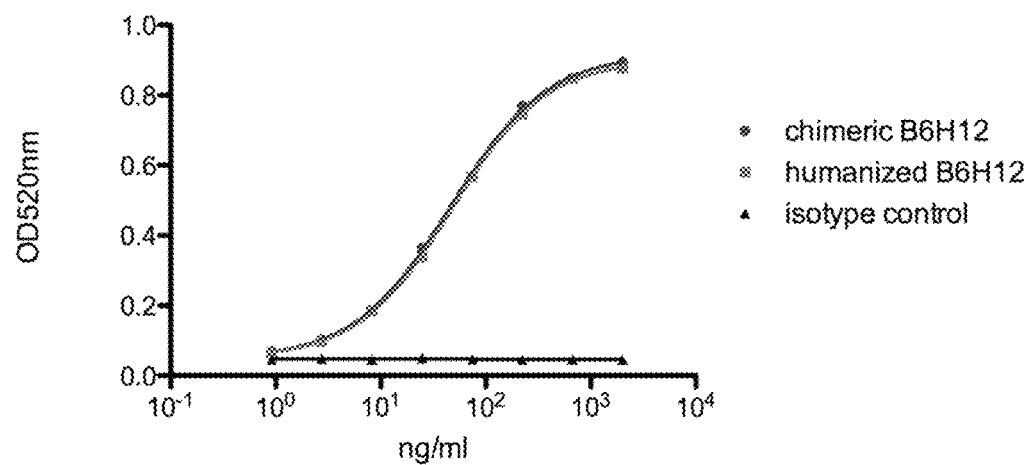
FIG. 6. Comparison of the binding of chimeric and humanized B6H12 antibodies to human CD47 by ELISA. Soluble CD47 binding activity was measured by ELISA as described in Materials and Methods. Bound antibody was detected with goat anti-human kappa conjugated to HRP, and signal was developed using OPT.

Next, the ability of humanized B6H12 to recognize human CD47 was examined. Human CD47-transfected YB2/0 cells, which have been shown to express membrane-bound CD47, were used for flow cytometry analysis. Humanized B6H12 bound CD47 expressed on the cell surface, and the binding activity was equivalent to the chimeric B6H12 antibody (FIG. 5). No binding was detected with B6H12 antibodies when untransfected YB2/0 cells were used. Similar results were also obtained when determining soluble CD47 binding by ELISA. In this assay, humanized B6H12 showed comparable binding activity to chimeric B6H12 antibody (FIG. 6).

Enabling of Phagocytosis by Chimeric and Humanized B6H12 Antibodies.

Figure 7:
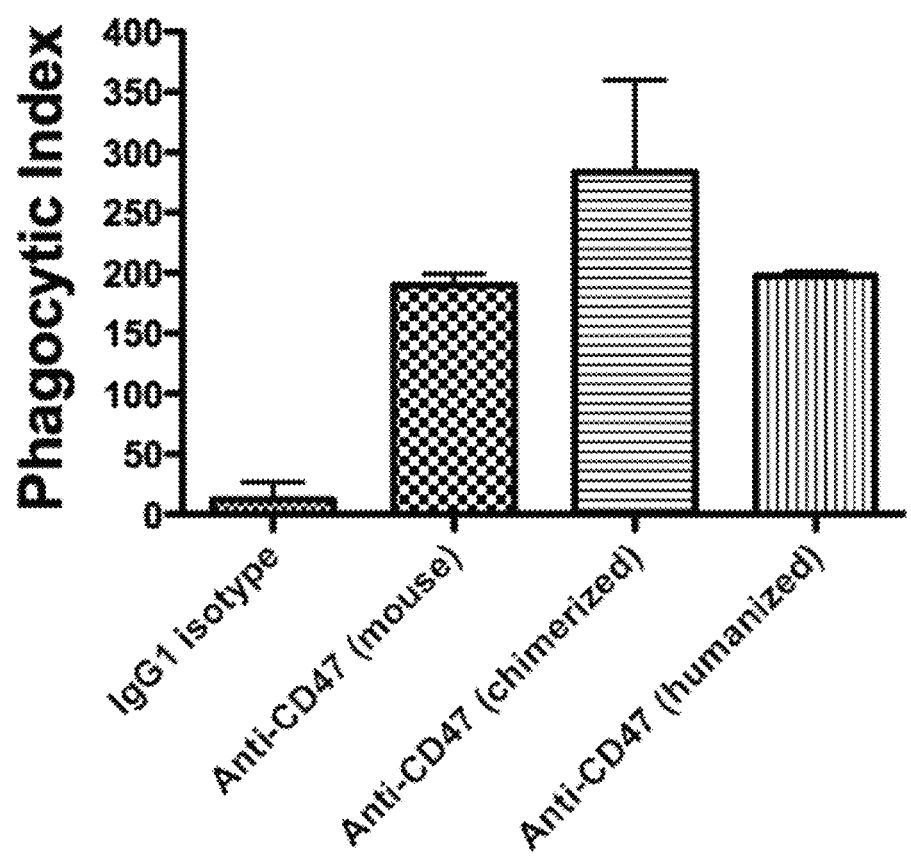
FIG. 7. Chimeric and humanized B6H12 antibody-mediated phagocytosis. CFSE-labeled HL-60 cells were incubated with mouse bone marrow-derived macrophages in a 4:1 target to effector cell ratio. 2 hours later, the macrophages were imaged by fluorescence microscopy to detect phagocytosis. The phagocytic index (number of target cells ingested per 100 macrophages) was determined for each condition in duplicate. Statistical comparison of each antibody to hIgG1 isotype control using Student's t-test showed all antibodies enabled a statistically significant increase in phagocytosis (p-values: mouse B6H12 antibody: 0.004; chimeric B6H12 antibody: 0.04; and humanized B6H12 antibody: 0.003.)

Mouse B6H12 antibody is known to block the interaction between CD47 and SIRPα, an inhibitory receptor expressed on macrophages, and thereby enable phagocytosis of the CD47-expressing cells. To examine the ability of chimeric and humanized B6H12 antibodies to enable phagocytosis, we conducted an in vitro phagocytosis assay. CFSE-labeled HL-60 cells were incubated with mouse bone marrow-derived macrophages for 2 hr in presence of control or B6H12 native, chimeric, or humanized antibody. Phagocytosis was assessed by counting the number of ingested CFSE-labeled HL-60 target cells within the mouse macrophages visualized by fluorescence microscopy. As shown in FIG. 7, both chimeric and humanized B6H12 efficiently enabled phagocytosis, at levels comparable to that of the native mouse B6H12 antibody. In contrast, an isotype control antibody did not trigger macrophage-mediated phagocytosis. These results demonstrate that chimeric and humanized B6H12 are able to function in a similar manner as the native mouse B6H12 antibody.

Thus far, antibodies generated against human CD47 have been mouse antibodies. A major disadvantage of using a mouse antibody in the treatment of human patients is the development of a human anti-mouse response (HAMA) in the patient. Accordingly, the need exists for improved therapeutic antibodies against CD47 that are less immunogenic. In the present study, we constructed and expressed chimeric and humanized antibodies engineered from variable regions of a mouse anti-human CD47 mAb (B6H12), which were fused to human immunoglobulin constant regions. SDS-PAGE analysis revealed that both the chimeric and humanized B6H12 antibodies are expressed as native IgG proteins composed of two pairs of heavy and light chains. Chimeric and mouse B6H12 antibodies competed each other for antigen binding (FIG. 3), indicating that chimeric B6H12 antibody retains the antigen binding of the mouse antibody and recognizes the same antigen epitope. Furthermore, humanized B6H12 antibody binds to both soluble and membrane-bound CD47 equivalently to the chimeric antibody (FIGS. 5 and 6). Chimeric and humanized B6H12 also showed efficient ability to enable phagocytosis as compared to the original mouse B6H12 antibody (FIG. 7). These results suggest that our engineered antibodies form functionally active IgGs.

Notably, in B6H12 antibody humanization, we utilized human VH-3-7 and VK3-11 as the basis for our design. However, mouse B6H12 also showed sequence homology to other family members in the human VH-3 and VK3 subgroups and to other variable domains outside these two subgroups. It is possible other frameworks may work just as well.

Antibodies exhibit four main effector functions: antibody-dependent cellular cytotoxicity (ADCC), phagocytosis, complement-dependent cytotoxicity (CDC), and half-life/clearance rate. Each of these effector functions is mediated through interaction with a specific set of receptors and cell types: ADCC and phagocytosis through interaction of cell-bound mAbs with Fc gamma receptors (FcγR), CDC through interaction of cell-bound mAbs with the series of soluble blood proteins that constitute the complement system (e.g. C1q, C3, C4, etc.), and half-life/clearance rate through binding of antibodies to the neonatal Fc receptor (FcRn). Activating antibodies, typically of the human IgG1 subclass, are dependent on an activating Fc-domain. Monoclonal antibodies that function by blocking a ligand-receptor interaction, however, can function without utilizing effector mechanisms. In these cases, effector functions may be disadvantageous as they may contribute to unwanted cytotoxicity. Unwanted agonism through crosslinking by FcR-expressing cells could trigger inappropriate activation of FcR-expressing cells and subsequent cytokine storm and associated toxic effects. Therefore, proper choice of IgG subclass or use of an IgG engineered to abrogate effector function is required. As we reported previously, murine B6H12 functioned as a blocking antibody, and a B6H12F(ab)'2 fragment showed similar efficacy to the full length murine B6H12 in in vitro phagocytosis assays. Thus, development of non-activating B6H12 monoclonal antibodies with fewer side effects is beneficial.

Many strategies have been reported to engineer non-activating antibodies. The use of antibody-based fragments lacking an Fc-domain provides the simplest way to avoid Fc-dependent effector mechanisms. From a manufacturing point of view, antibody-based fragments represent an attractive strategy as high yields are routinely obtained in well-characterized and cost-effective lower eukaryotic and prokaryotic expression systems. Recombinant antibody technologies have made monovalent (e.g. Fab, scFv, nanobodies, and dAbs), bivalent (e.g. F(ab')$_2$, diabodies, and minibodies) and multivalent (e.g. triabodies and pentabodies) formats available. These approaches have already resulted in FDA-approved therapeutics, and several others are undergoing clinical evaluation, illustrating the confidence in this approach. However, removal of the Fc-domain will dramatically change the pharmacokinetic properties of antibody-based fragments and make antibody purification less convenient. Without an Fc-domain, renal clearance is the predominant mechanism influencing serum half-life and antibody-based fragments smaller than ~50-70 kDa are subject to this route of elimination. Increasing the apparent molecular size of small antibody fragments, for instance through linkage to polyethylene glycol (PEG) and human serum albumin (HSA), represents an alternative strategy to increase circulation time and to improve their pharmacokinetic properties.

Combinations of therapeutic antibodies are also increasingly being used that may bring the additional benefit of targeting multiple epitopes or antigens. Combinations may be more effective against disease targets that are commonly heterogeneous and may thereby limit resistance or escape. We have demonstrated synergy and cure with B6H12 in combination with rituximab in human NHL xenotransplantation models. Our findings suggest that combination therapy with B6H12 is a promising new treatment modality for NHL. Meanwhile, over the last few years, the concept of bispecific antibody (BsAb)-mediated tumor cell killing has been studied extensively both in preclinical models and clinical trials. BsAbs share two different antigen-recognizing moieties within one molecule. Based on our data, B6H12 will synergize with additional FcR-engaging antibodies to eliminate target cells. This synergy may be recapitulated in B6H12BsAbs reactive with CD47 on one hand and an additional surface antigen on a tumor target cell on the other. Such a reagent may focus immune effector functions towards the target cells.

In summary, we have developed therapeutic antibodies based on the mouse monoclonal antibody B6H12 directed against human CD47, by using methods to create a mouse/human chimeric antibody and a humanized antibody. The chimeric and humanized B6H12 antibodies retain the ability to specifically bind CD47 and are able to induce phagocytosis in vitro. These antibodies may be less immunogenic, and thus are more suitable as potential clinical therapeutics.

Example 2

Cloning of Mouse 5F9 and 8B6 Variable Regions

Using universal antibody primers, DNA fragments encoding heavy and light chain variable regions were successfully cloned from anti-CD47 hybridomas 5F9 and 8B6. Multiple clones of each V gene product were sequenced to monitor PCR-induced errors. The VH and VL sequences of 5F9 are shown in FIGS. 9A and 9B, respectively. DNA sequence analysis for products demonstrated that the heavy chain of 5F9 uses a V segment of the Igh-VJ558 VH1 family, and that the light chain belongs to the IGKV1 subgroup. The VH and VL sequences of 8B6 are shown in FIGS. 10A and 10B, respectively. DNA sequence analysis for products demonstrated that the heavy chain of 8B6 uses a V segment of the Igh-VJ558 VH1 family, and that the light chain belongs to the IGKV23 subgroup. The heavy chain variable regions comprise CDR1, CDR2, and CDR3 sequences; and the light chain variable regions comprise CDR1, CDR2, and CDR3 sequences (FIGS. 9 and 10).

Figure 11:
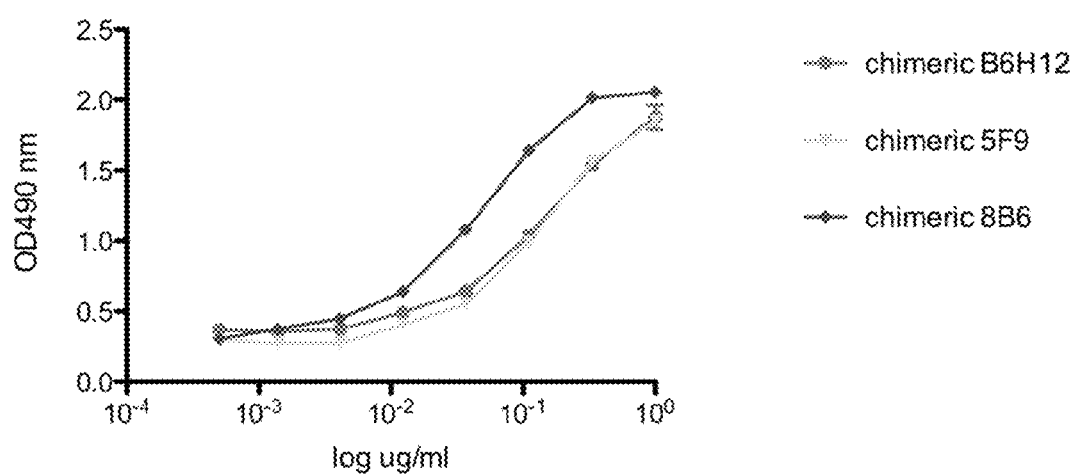
FIG. 11. Comparison of the binding of chimeric 5F9 and 8B6 antibodies to human CD47 by ELISA. Soluble CD47 binding activity was measured by an ELISA assay as described previously. Bound antibody was detected with goat anti-human kappa conjugated to HRP, and signal was developed using OPT.

CD47 binding activities of chimeric 5F9 and 8B6. Chimeric 5F9 and 8B6 were constructed and expressed. Purified antibodies were analyzed by SDS-PAGE, demonstrating that native IgG antibodies were formed for both. Then, binding activities of chimeric 5F9 and 8B6 were tested using ELISA by coating human CD47 soluble protein in the 96-well plates. As shown in FIG. 11, both chimeric 5F9 and 8B6 bound the antigen at comparable levels to that of chimeric B6H12 antibody.

Antibody humanization and characterization of 5F9. In order to select human antibody framework regions (FR) to be used as templates for CDR-grafting, the mouse 5F9 VL and VH regions were compared with those of human germline sequences. The FRs of the mouse 5F9 VL region were found to have the highest homology with IGKV2 subgroup. The FRs of the mouse 5F9 VH region exhibited the highest homology with human VH-1 subgroup. Identical residues in the FRs were retained and non-identical residues were either retained or substituted based on molecular modeling. Three versions of each humanized VH and VL were designed. Sequence alignments of each version together with human germline sequences are indicated in FIG. 12.

Figure 13:
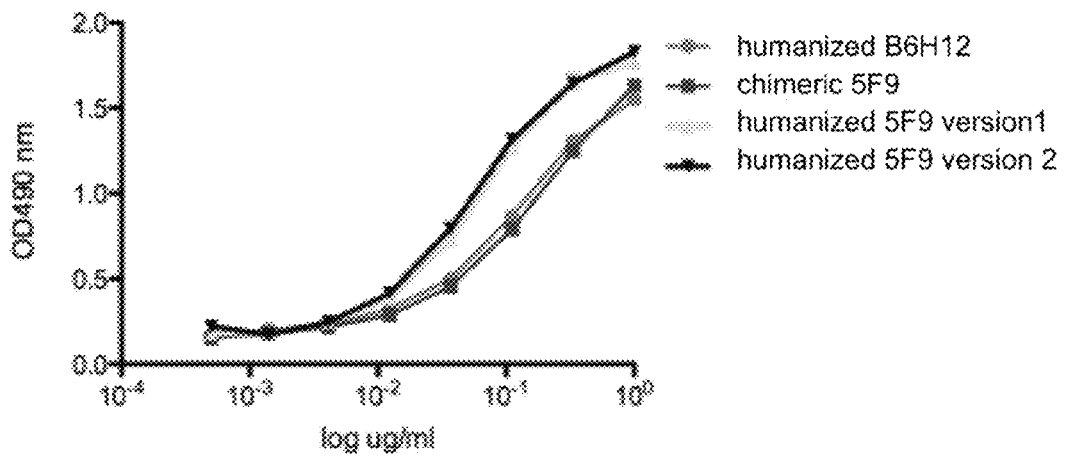
FIG. 13. Comparison of the binding of humanized and chimeric 5F9 antibodies to human CD47 by ELISA. Soluble CD47 binding activity was measured by an ELISA assay as described previously. Bound antibody was detected with goat anti-human kappa conjugated to HRP, and signal was developed using OPT.

Different versions of humanized 5F9 heavy and light chains were transfected in combinations, yielding different versions of humanized 5F9. Then, the ability of humanized 5F9 antibodies to recognize CD47 was examined. As shown in FIG. 13, both version 1 and version 2 of humanized 5F9 bound well to soluble CD47. Isotype control antibody did not show any binding activity. These results demonstrate that humanized 5F9 retained binding capability to the human CD47 antigen.

Figure 14:
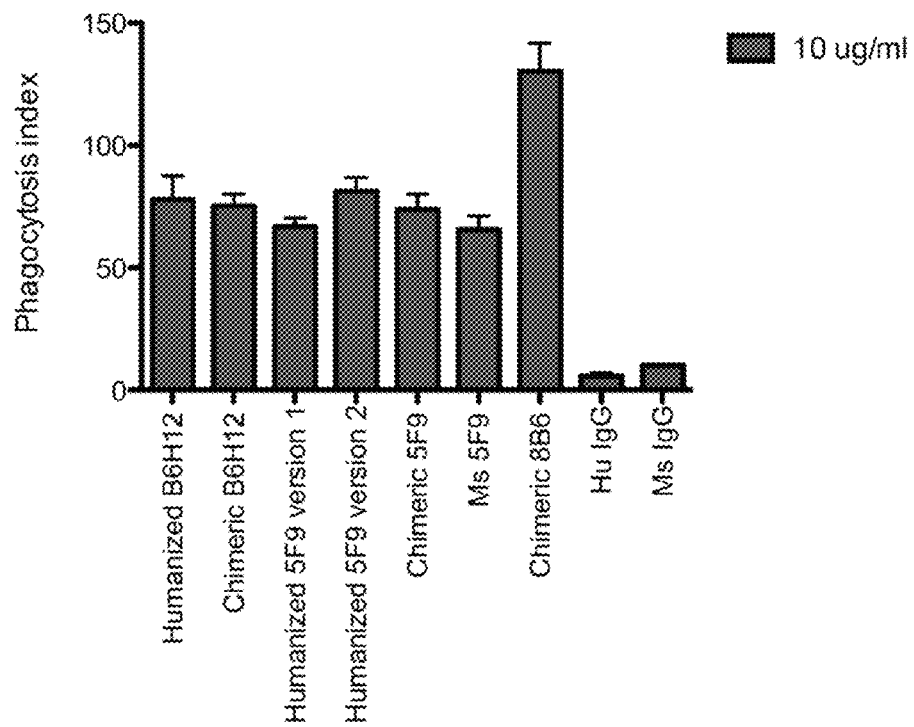
FIG. 14. Phagocytosis induced by antibodies of 5F9 and 8B6. HL-60 cells were used as target cells and incubated with human peripheral blood-derived macrophages in a 4:1 target to effector cell ratio. Each condition was done in duplicate.
Figure 15:
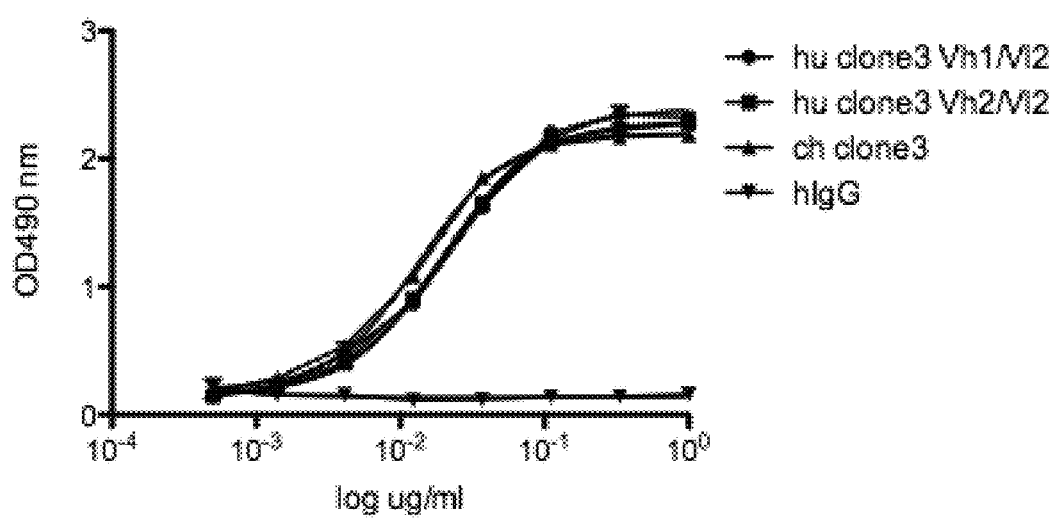
FIG. 15. ELISA binding to huCD47-mFc fusion with C3 antibody.
Figure 16:
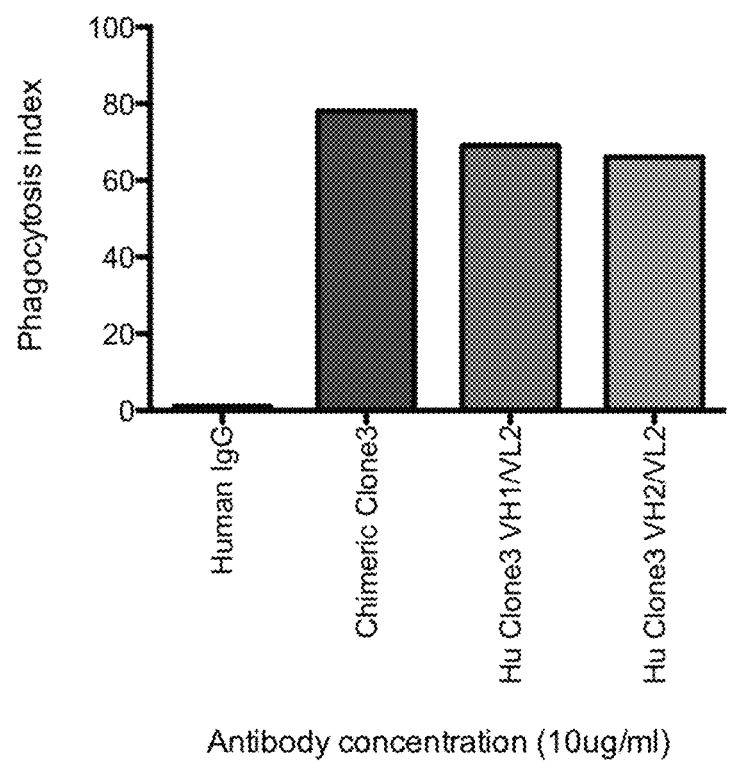
FIG. 16. In vitro phagocytosis against HL-60 with C3 antibody.

Phagocytosis induced by 5F9 and 8B6 antibodies. B6H12 antibody is known to block the interaction between CD47 and SIRPα that is expressed on macrophages and in turn to activate macrophages for phagocytic response. To examine 5F9 and 8B6 antibodies ability to induce phagocytosis, we incubated the antibodies with human peripheral blood-derived macrophages and HL-60 target cells for 2 hr, and assessed phagocytosis by counting the number of ingested CFSE-labeled HL-60 cells under a microscope. As shown in FIG. 14, both mouse and chimeric 5F9 were able to elicit phagocytosis efficiently, as did chimeric 8B6. Moreover, humanized 5F9 antibodies also displayed effective phagocytic activity. In contrast, isotype control antibodies did not trigger macrophage-mediated phagocytosis. These results demonstrate that 5F9 and 8B6 are able to function in a similar manner as B6H12 antibody.

What is claimed is:

1. An isolated chimeric or humanized antibody that specifically binds to human CD47 comprising a variable heavy (VH) region containing the VH complementarity regions, CDR1, CDR2 and CDR3, respectively set forth in SEQ ID NO: 20, 20 and 22; and a variable light (VL) region containing the VL complementarity regions, CDR1, CDR2 and CDR3, respectively set forth in SEQ ID NO:23, 24 and 25.

2. The antibody of claim 1, wherein said variable light (VL) region comprises the amino acid sequence selected from the group consisting of the SEQ ID NO: 41, SEQ ID NO: 42 and SEQ ID NO: 43.

3. The antibody of claim 1, wherein said variable heavy (VH) region comprises the amino acid sequence selected from the group consisting of the SEQ ID NO: 36, SEQ ID NO: 37 and SEQ ID NO: 38.

4. The antibody of claim 1, wherein the antibody does not activate CD47 upon binding.

5. The antibody of claim 4, wherein the antibody is a humanized monoclonal antibody.

6. The antibody of claim 4, wherein the antibody is a chimeric antibody.

7. A pharmaceutical composition comprising an antibody set forth in claim 1.

8. A pharmaceutical composition comprising an antibody set forth in claim 1, and a pharmaceutically acceptable excipient.

* * * * *

UNITED STATES PATENT AND TRADEMARK OFFICE
CERTIFICATE OF CORRECTION

PATENT NO. : 9,017,675 B2
APPLICATION NO. : 13/675274
DATED : April 28, 2015
INVENTOR(S) : Jie Liu et al.

Page 1 of 1

It is certified that error appears in the above-identified patent and that said Letters Patent is hereby corrected as shown below:

In the Claims

In Claim 1, Column 61, Line 54:
Delete "SEQ ID NO:20, 20 and 22" and replace with --SEQ ID NO:20, 21 and 22--

Signed and Sealed this
Twelfth Day of May, 2020

Andrei Iancu
*Director of the United States Patent and Trademark Office*

```
SEQUENCE LISTING

<160> NUMBER OF SEQ ID NOS: 78

<210> SEQ ID NO 1
<211> LENGTH: 118
<212> TYPE: PRT
<213> ORGANISM: Mus musculus

<400> SEQUENCE: 1

Glu Val Gln Leu Val Glu Ser Gly Gly Asp Leu Val Lys Pro Gly Gly
 1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
        115

<210> SEQ ID NO 2
<211> LENGTH: 107
<212> TYPE: PRT
<213> ORGANISM: Mus musculus

<400> SEQUENCE: 2

Asp Ile Val Met Thr Gln Ser Pro Ala Thr Leu Ser Val Thr Pro Gly
 1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80
```

Glu Asp Val Gly Val Tyr Tyr Cys Gln Asn Gly His Gly Phe Pro Arg
            85                  90                  95

Thr Phe Gly Gly Gly Thr Lys Leu Glu Ile Lys
            100                 105

<210> SEQ ID NO 3
<211> LENGTH: 5
<212> TYPE: PRT
<213> ORGANISM: Artificial Sequence
<220> FEATURE:
<223> OTHER INFORMATION: B6H12 heavy chain CDR1

<400> SEQUENCE: 3

Gly Tyr Gly Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: B6H12 heavy chain CDR2

<400> SEQUENCE: 4

Thr Ile Thr Ser Gly Gly Thr Tyr Thr Tyr Tyr Pro Asp Ser Val Lys
1               5                   10                  15

Gly

<210> SEQ ID NO 5
<211> LENGTH: 9
<212> TYPE: PRT
<213> ORGANISM: Artificial Sequence
<220> FEATURE:
<223> OTHER INFORMATION: B6H12 heavy chain CDR3

<400> SEQUENCE: 5

Ser Leu Ala Gly Asn Ala Met Asp Tyr
1               5

<210> SEQ ID NO 6
<211> LENGTH: 11
<212> TYPE: PRT
<213> ORGANISM: Artificial Sequence
<220> FEATURE:
<223> OTHER INFORMATION: B6H12 light chain CDR1

<400> SEQUENCE: 6

Arg Ala Ser Gln Thr Ile Ser Asp Tyr Leu His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: B6H12 light chain CDR2

<400> SEQUENCE: 7

Phe Ala Ser Gln Ser Ile Ser
1               5

<210> SEQ ID NO 8
<211> LENGTH: 9
<212> TYPE: PRT
<213> ORGANISM: Artificial Sequence
<220> FEATURE:
<223> OTHER INFORMATION: B6H12 light chain CDR3

<400> SEQUENCE: 8

Gln Asn Gly His Gly Phe Pro Arg Thr
 1               5

<210> SEQ ID NO 9
<211> LENGTH: 354
<212> TYPE: DNA
<213> ORGANISM: Artificial Sequence
<220> FEATURE:
<223> OTHER INFORMATION: Humanized B6H12 heavy chain

<400> SEQUENCE: 9

```
gaggtgcagc tggtggagtc tgggggaggc ttggtccagc ctggggggtc cctgagactc      60
tcctgtgcag cctctggatt cacctttagt ggctatggca tgagctgggt ccgccaggct     120
ccagggaagg gctggagtg gtggccacc ataactagtg gtggaactta cacctactat     180
ccagactctg tgaagggccg attcaccatc tccagagaca cgccaagaa ctcactgtat     240 ctgcaaatga acagcctgag agccgaggac acggctgtgt attactgtgc gagatccctc     300
gcgggaaatg ctatggacta ctggggccaa ggaaccctgg tcaccgtctc ctca           354
```

<210> SEQ ID NO 10
<211> LENGTH: 321
<212> TYPE: DNA
<213> ORGANISM: Artificial Sequence
<220> FEATURE:
<223> OTHER INFORMATION: Humanized B6H12 light chain

<400> SEQUENCE: 10

```
gaaattgtgt tgacacagtc tccagccacc ctgtctttgt ctccagggga aagagccacc      60
ctctcctgca gggccagtca gactattagc gactacttac actggtacca acagaaacct     120
ggccaggctc ccaggctcct catcaaattt gcatcccaat ccatttctgg catcccagcc     180
aggttcagtg gcagtgggtc tgggacagac ttcactctca ccatcagcag cctagagcct     240
gaagattttg cagtttatta ctgtcagaat ggtcacggct tcctcggac gttcggccaa     300 gggaccaagg tggaaatcaa a                                                 321
```

<210> SEQ ID NO 11
<211> LENGTH: 118
<212> TYPE: PRT
<213> ORGANISM: Artificial Sequence
<220> FEATURE:
<223> OTHER INFORMATION: Humanized B6H12 VH

<400> SEQUENCE: 11

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Humanized B6H12 VL

<400> SEQUENCE: 12

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Thr Ile Ser Asp Tyr
            20                  25                  30

Leu His Trp Tyr Gln Gln Lys Pro Gly Gln Ala Pro Arg Leu Leu Ile
        35                  40                  45

Lys Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Gly Phe Pro Arg
                85                  90                  95

Thr Phe Gly Gln Gly Thr Lys Val Glu Ile Lys
            100                 105

<210> SEQ ID NO 13
<211> LENGTH: 411
<212> TYPE: DNA
<213> ORGANISM: Mus musculus

<400> SEQUENCE: 13
atgaacttcg ggctcagctt gattttcctt gccctcattt taaaaggtgt ccagtgtgag     60
gtgcagctgg tggagtctgg gggagactta gtgaagcctg agggtccct gaaactctcc    120 tgtgcagcct ctggattcac tttcagtggc tatggcatgt cttgggttcg ccagactcca    180
gacaagaggc tggagtgggt cgcaaccatt actagtggtg gtacttacac ctactatcca    240
gacagtgtga aggggcgatt caccatctcc agagacaatg ccaagaacac cctgtacctg    300
caaatagaca gtctgaagtc tgaggataca gccatatatt tctgtgcaag atccctcgcg    360
ggaaatgcta tggactactg ggtcaagga acctcagtca ccgtctcctc a              411

<210> SEQ ID NO 14
<211> LENGTH: 381
<212> TYPE: DNA
<213> ORGANISM: Mus musculus

<400> SEQUENCE: 14
atggtgtcca cttctcagct ccttggactt ttgcttttct ggacttcagc ctccagatgt     60
gacattgtga tgactcagtc tccagccacc ctgtctgtga ctccaggaga tagagtctct    120
ctttcctgca gggccagcca gactattagc gactacttac actggtatca acaaaaatca    180
catgagtctc caaggcttct catcaaattt gcttcccaat ccatttctgg gatccctcc     240 aggttcagtg gcagtggatc aggctcagat ttcactctca gtatcaacag tgtggaacct    300

```
gaagatgttg gagtgtatta ctgtcaaaat ggtcacggct ttcctcggac gttcggtgga    360
ggcaccaagc tggaaatcaa a                                              381
```

<210> SEQ ID NO 15
<211> LENGTH: 1
<212> TYPE: PRT
<213> ORGANISM: Artificial Sequence
<220> FEATURE:
<223> OTHER INFORMATION: Humanized antibody polypeptide

<400> SEQUENCE: 15

Ala
 1

<210> SEQ ID NO 16
<211> LENGTH: 1
<212> TYPE: PRT
<213> ORGANISM: Artificial Sequence
<220> FEATURE:
<223> OTHER INFORMATION: Humanized antibody polypeptide

<400> SEQUENCE: 16

Ala
 1

<210> SEQ ID NO 17
<211> LENGTH: 118
<212> TYPE: PRT
<213> ORGANISM: Artificial Sequence
<220> FEATURE:
<223> OTHER INFORMATION: Humanized B6H12 VH

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Gly Asn Ala Met Asp Tyr Trp Gly Gln Gly Thr
            100                 105                 110

Leu Val Thr Val Ser Ser
        115

<210> SEQ ID NO 18
<211> LENGTH: 116
<212> TYPE: PRT
<213> ORGANISM: Artificial Sequence
<220> FEATURE:
<223> OTHER INFORMATION: 5F9 heavy chain variable region

<400> SEQUENCE: 18

Gln Val Gln Leu Gln Gln Pro Gly Ala Glu Leu Val Lys Pro Gly Ala
 1               5                  10                  15

Ser Val Met Met Ser Cys Lys Ala Ser Gly Tyr Thr Phe Thr Asn Tyr
            20                  25                  30

```
Asn Met His Trp Val Lys Gln Thr Pro Gly Gln Gly Leu Glu Trp Ile
         35                  40                  45

Gly Thr Ile Tyr Pro Gly Asn Asp Asp Thr Ser Tyr Asn Gln Lys Phe
     50                  55                  60

Lys Asp Lys Ala Thr Leu Thr Ala Asp Lys Ser Ser Ser Ala Ala Tyr
 65                  70                  75                  80

Met Gln Leu Ser Ser Leu Thr Ser Glu Asp Ser Ala Val Tyr Tyr Cys
                 85                  90                  95

Ala Arg Gly Gly Tyr Arg Ala Met Asp Tyr Trp Gly Gln Gly Thr Ser Val
             100                 105                 110

Thr Val Ser Ser
         115
```

<210> SEQ ID NO 19
<211> LENGTH: 112
<212> TYPE: PRT
<213> ORGANISM: Artificial Sequence
<220> FEATURE:
<223> OTHER INFORMATION: 5F9 light chain variable region

<400> SEQUENCE: 19

```
Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val Tyr Ser
             20                  25                  30

Asn Gly Asn Thr Tyr Leu Gly Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr His Cys Phe Gln Gly
                 85                  90                  95

Ser His Val Pro Tyr Thr Phe Gly Gly Gly Thr Lys Val Glu Ile Lys
             100                 105                 110
```

<210> SEQ ID NO 20
<211> LENGTH: 5
<212> TYPE: PRT
<213> ORGANISM: Artificial Sequence
<220> FEATURE:
<223> OTHER INFORMATION: 5F9 heavy chain CDR1

<400> SEQUENCE: 20

```
Asn Tyr Asn Met His
 1               5
```

<210> SEQ ID NO 21
<211> LENGTH: 17
<212> TYPE: PRT
<213> ORGANISM: Artificial Sequence
<220> FEATURE:
<223> OTHER INFORMATION: 5F9 heavy chain CDR2

<400> SEQUENCE: 21

```
Thr Ile Tyr Pro Gly Asn Asp Asp Thr Ser Tyr Asn Gln Lys Phe Lys
 1               5                  10                  15

Asp
```

-continued

<210> SEQ ID NO 22
<211> LENGTH: 8
<212> TYPE: PRT
<213> ORGANISM: Artificial Sequence
<220> FEATURE:
<223> OTHER INFORMATION: 5F9 heavy chain CDR3

<400> SEQUENCE: 22

Gly Gly Tyr Arg Ala Met Asp Tyr
 1               5

<210> SEQ ID NO 23
<211> LENGTH: 16
<212> TYPE: PRT
<213> ORGANISM: Artificial Sequence
<220> FEATURE:
<223> OTHER INFORMATION: 5F9 light chain CDR1

<400> SEQUENCE: 23

Arg Ser Ser Gln Ser Ile Val Tyr Ser Asn Gly Asn Thr Tyr Leu Gly
 1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: 5F9 light chain CDR2

<400> SEQUENCE: 24

Lys Val Ser Asn Arg Phe Ser
 1               5

<210> SEQ ID NO 25
<211> LENGTH: 9
<212> TYPE: PRT
<213> ORGANISM: Artificial Sequence
<220> FEATURE:
<223> OTHER INFORMATION: 5F9 light chain CDR3

<400> SEQUENCE: 25

Phe Gln Gly Ser His Val Pro Tyr Thr
 1               5

<210> SEQ ID NO 26
<211> LENGTH: 120
<212> TYPE: PRT
<213> ORGANISM: Mus musculus

<400> SEQUENCE: 26

Glu Val Gln Leu Gln Gln Ser Gly Pro Glu Leu Val Lys Pro Gly Ala
 1               5                   10                  15

Ser Val Lys Met Ser Cys Lys Ala Ser Gly Tyr Thr Phe Thr Thr Tyr
                20                  25                  30

Val Val His Trp Val Lys Gln Thr Pro Gly Gln Gly Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Phe Ser Ser Leu Thr Ser Glu Asp Ser Ala Val Tyr Tyr Cys
                85                  90                  95

Val Arg Gly Tyr Tyr Arg Tyr Gly Tyr Thr Met Asp Tyr Trp Gly Gln
            100                 105                 110

Gly Thr Ser Val Thr Val Ser Ser
        115                 120

<210> SEQ ID NO 27
<211> LENGTH: 107
<212> TYPE: PRT
<213> ORGANISM: Mus musculus

<400> SEQUENCE: 27

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Asn Phe Ser Asp Tyr
            20                  25                  30

Leu His Trp Tyr Gln Gln Lys Ser His Glu Ser Pro Arg Leu Leu Ile
        35                  40                  45

Lys Tyr Val Ser His Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Gly Gly Thr Lys Leu Glu Ile Lys
            100                 105

<210> SEQ ID NO 28
<211> LENGTH: 5
<212> TYPE: PRT
<213> ORGANISM: Artificial Sequence
<220> FEATURE:
<223> OTHER INFORMATION: 8B6 heavy chain CDR1

<400> SEQUENCE: 28

Thr Tyr Val Val His
1               5

<210> SEQ ID NO 29
<211> LENGTH: 17
<212> TYPE: PRT
<213> ORGANISM: Artificial Sequence
<220> FEATURE:
<223> OTHER INFORMATION: 8B6 heavy chain CDR2

<400> SEQUENCE: 29

Tyr Ile Asn Pro Tyr Asn Asp Gly Thr Lys Tyr Asn Glu Lys Phe Lys
1               5                   10                  15

Gly

<210> SEQ ID NO 30
<211> LENGTH: 11
<212> TYPE: PRT
<213> ORGANISM: Artificial Sequence
<220> FEATURE:
<223> OTHER INFORMATION: 8B6 heavy chain CDR3

<400> SEQUENCE: 30

Gly Tyr Tyr Arg Tyr Gly Tyr Thr Met Asp Tyr
1               5                   10

```
<210> SEQ ID NO 31
<211> LENGTH: 11
<212> TYPE: PRT
<213> ORGANISM: Artificial Sequence
<220> FEATURE:
<223> OTHER INFORMATION: 8B6 light chain CDR1

<400> SEQUENCE: 31

Arg Ala Ser Gln Asn Phe Ser Asp Tyr Leu His
 1               5                  10

<210> SEQ ID NO 32
<211> LENGTH: 7
<212> TYPE: PRT
<213> ORGANISM: Artificial Sequence
<220> FEATURE:
<223> OTHER INFORMATION: 8B6 light chain CDR2

<400> SEQUENCE: 32

Tyr Val Ser His Ser Ile Ser
 1               5

<210> SEQ ID NO 33
<211> LENGTH: 9
<212> TYPE: PRT
<213> ORGANISM: Artificial Sequence
<220> FEATURE:
<223> OTHER INFORMATION: 8B6 light chain CDR3

<400> SEQUENCE: 33

Gln Asn Gly His Ser Phe Pro Pro Thr
 1               5

<210> SEQ ID NO 34
<211> LENGTH: 107
<212> TYPE: PRT
<213> ORGANISM: Artificial Sequence
<220> FEATURE:
<223> OTHER INFORMATION: Humanized antibody 3-11-1

<400> SEQUENCE: 34

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 35
<211> LENGTH: 109
<212> TYPE: PRT
<213> ORGANISM: Artificial Sequence
<220> FEATURE:
<223> OTHER INFORMATION: Humanized antibody 3-07-4
```

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
            100                 105

<210> SEQ ID NO 36
<211> LENGTH: 117
<212> TYPE: PRT
<213> ORGANISM: Artificial Sequence
<220> FEATURE:
<223> OTHER INFORMATION: Humanized antibody hu5F9-vh1

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Gly Leu Glu Trp Ile
        35                  40                  45

Gly Thr Ile Tyr Pro Gly Asn Asp Asp Thr Ser Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Humanized antibody hu5F9-vh2

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

```
Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Arg Ala Met Asp Tyr Trp Gly Gln Gly Thr Leu
                100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: Humanized antibody hu5F9-vh3

<400> SEQUENCE: 38

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Asn Met His Trp Val Arg Gln Ala Pro Gly Gln Arg Leu Glu Trp Ile
             35                  40                  45

Gly Thr Ile Tyr Pro Gly Asn Asp Asp Thr Ser Tyr Asn Gln Lys Phe
    50                  55                  60

Lys Asp Arg Ala Thr Leu Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Arg Ala Met Asp Tyr Trp Gly Gln Gly Thr Leu
                100                 105                 110

Val Thr Val Ser Ser
        115

<210> SEQ ID NO 39
<211> LENGTH: 98
<212> TYPE: PRT
<213> ORGANISM: Artificial Sequence
<220> FEATURE:
<223> OTHER INFORMATION: Humanized antibody IGHV1-03-01

<400> SEQUENCE: 39

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Ala Met His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

-continued

```
<210> SEQ ID NO 40
<211> LENGTH: 98
<212> TYPE: PRT
<213> ORGANISM: Artificial Sequence
<220> FEATURE:
<223> OTHER INFORMATION: Humanized antibody IGHV1-46-03

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 41
<211> LENGTH: 112
<212> TYPE: PRT
<213> ORGANISM: Artificial Sequence
<220> FEATURE:
<223> OTHER INFORMATION: Humanized antibody hu5F9-vl1

<400> SEQUENCE: 41

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Phe Gln Gly
                85                  90                  95

Ser His Val Pro Tyr Thr Phe Gly Gly Gly Thr Lys Val Glu Ile Lys
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Humanized antibody hu5F9-vl2

<400> SEQUENCE: 42

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45
```

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Tyr Thr Phe Gly Gln Gly Thr Lys Leu Glu Ile Lys
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Humanized antibody hu5F9-vl3

<400> SEQUENCE: 43

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr His Cys Phe Gln Gly
                 85                  90                  95

Ser His Val Pro Tyr Thr Phe Gly Gln Gly Thr Lys Leu Glu Ile Lys
            100                 105                 110

<210> SEQ ID NO 44
<211> LENGTH: 100
<212> TYPE: PRT
<213> ORGANISM: Artificial Sequence
<220> FEATURE:
<223> OTHER INFORMATION: Humanized antibody IGKV2-28-01

<400> SEQUENCE: 44

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

```
<210> SEQ ID NO 45
<211> LENGTH: 43
<212> TYPE: DNA
<213> ORGANISM: Artificial Sequence
<220> FEATURE:
<223> OTHER INFORMATION: Synthetic primer

<400> SEQUENCE: 45
cagacccgtc gacatgaact cgggctcag cttgattttc ctt                         43

<210> SEQ ID NO 46
<211> LENGTH: 45
<212> TYPE: DNA
<213> ORGANISM: Artificial Sequence
<220> FEATURE:
<223> OTHER INFORMATION: Synthetic primer

<400> SEQUENCE: 46
gcccttggtg ctagctgagg agacggtgac tgaggttcct tgacc                      45

<210> SEQ ID NO 47
<211> LENGTH: 45
<212> TYPE: DNA
<213> ORGANISM: Artificial Sequence
<220> FEATURE:
<223> OTHER INFORMATION: Synthetic primer

<400> SEQUENCE: 47
cgccatcaca gatctatggt gtccacttct cagctccttg gactt                      45

<210> SEQ ID NO 48
<211> LENGTH: 45
<212> TYPE: DNA
<213> ORGANISM: Artificial Sequence
<220> FEATURE:
<223> OTHER INFORMATION: Synthetic primer

<400> SEQUENCE: 48
tgcagccacc gtacgtttga tttccagctt ggtgcctcca ccgaa                      45

<210> SEQ ID NO 49
<211> LENGTH: 348
<212> TYPE: DNA
<213> ORGANISM: Artificial Sequence
<220> FEATURE:
<223> OTHER INFORMATION: Clone 3 Heavy

<400> SEQUENCE: 49
caggtccaac tgcagcagtc tggggctgaa ctggtgaagc ctggggcttc agtgaagttg      60
tcctgcaagg cttctggcta caccttcacc aactactata tattctgggt gaaagagagg     120
cctggacaag gccttgagtg gattggagac attaatccta gtaatggtga tactaacttc     180
aatgagaagt tcaagatcaa ggccacactg actgtagaca atcctccag cacaacatac      240 atgcaactca acagcctgac atctgaggac tctgcggtct atttctgtac aagagggggt     300
tatactatgg actactgggg tcaaggaacc tcagtcaccg tctcctca                  348

<210> SEQ ID NO 50
<211> LENGTH: 116
<212> TYPE: PRT
<213> ORGANISM: Artificial Sequence
<220> FEATURE:
<223> OTHER INFORMATION: Clone 3 Heavy
```

<400> SEQUENCE: 50

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Tyr Ile Phe Trp Val Lys Glu Arg Pro Gly Gln Gly Leu Glu Trp Ile
        35                  40                  45

Gly Asp Ile Asn Pro Ser Asn Gly Asp Thr Asn Phe Asn Glu Lys Phe
    50                  55                  60

Lys Ile Lys Ala Thr Leu Thr Val Asp Lys Ser Ser Ser Thr Thr Tyr
65                  70                  75                  80

Met Gln Leu Asn Ser Leu Thr Ser Glu Asp Ser Ala Val Tyr Phe Cys
                85                  90                  95

Thr Arg Gly Gly Tyr Thr Met Asp Tyr Trp Gly Gln Gly Thr Ser Val
            100                 105                 110

Thr Val Ser Ser
            115

<210> SEQ ID NO 51
<211> LENGTH: 336
<212> TYPE: DNA
<213> ORGANISM: Artificial Sequence
<220> FEATURE:
<223> OTHER INFORMATION: Clone 3 Light

<400> SEQUENCE: 51
gatgttgtga tgacccaaac tccactctcc ctgcctgtca gtcttggaga tcaagcctcc      60
atctcttgca gatctagtca gagccttgta cacagtaatg gaaacaccta tttcattgg     120 tacgtgcaga agccaggcca gtctccaaaa ctcctgatct acaaagtttc ctaccgattt     180
tctggggtcc cagacaggtt cagtggcagt gggtcaggga cagatttcac actcaagatc     240
agcagagtgg aggctgagga tctgggagtt tatttctgtt ctcaaagtac acatgttcct     300
cggacgttcg gtggaggcac caagctggaa atcaaa                              336

<210> SEQ ID NO 52
<211> LENGTH: 112
<212> TYPE: PRT
<213> ORGANISM: Artificial Sequence
<220> FEATURE:
<223> OTHER INFORMATION: Clone 3 Light

<400> SEQUENCE: 52

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Phe His Trp Tyr Val Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110

<210> SEQ ID NO 53
<211> LENGTH: 348
<212> TYPE: DNA
<213> ORGANISM: Artificial Sequence
<220> FEATURE:
<223> OTHER INFORMATION: Humanized Clone 3 Heavy (A)

<400> SEQUENCE: 53

```
caggtgcagc tggtgcagtc tggggctgag gtgaagaagc ctggggcctc agtgaaggtt      60
tcctgcaagg catctggata caccttcacc aactactata tattctgggt gcgacaggcc     120
cctggacaag ggcttgagtg gattggagac attaatccta gtaatggtga tactaacttc     180
aatgagaagt tcaagatcaa ggccacactg accgtagaca atccacgag cacaacatac      240
atggagctga gcagcctgag atctgaggac acggccgtgt attactgtac aagagggggt     300
tatactatgg actactgggg ccaaggaacc ctggtcaccg tctcctca               348
```

<210> SEQ ID NO 54
<211> LENGTH: 116
<212> TYPE: PRT
<213> ORGANISM: Artificial Sequence
<220> FEATURE:
<223> OTHER INFORMATION: Humanized Clone 3 Heavy (A)

<400> SEQUENCE: 54

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
             20                  25                  30

Tyr Ile Phe Trp Val Arg Gln Ala Pro Gly Gln Gly Leu Glu Trp Ile
         35                  40                  45

Gly Asp Ile Asn Pro Ser Asn Gly Asp Thr Asn Phe Asn Glu Lys Phe
     50                  55                  60

Lys Ile Lys Ala Thr Leu Thr Val Asp Lys Ser Thr Ser Thr Thr Tyr
 65                  70                  75                  80

Met Glu Leu Ser Ser Leu Arg Ser Glu Asp Thr Ala Val Tyr Tyr Cys
                 85                  90                  95

Thr Arg Gly Gly Tyr Thr Met Asp Tyr Trp Gly Gln Gly Thr Leu Val
            100                 105                 110

Thr Val Ser Ser
        115
```

<210> SEQ ID NO 55
<211> LENGTH: 348
<212> TYPE: DNA
<213> ORGANISM: Artificial Sequence
<220> FEATURE:
<223> OTHER INFORMATION: Humanized Clone 3 Heavy (B)

<400> SEQUENCE: 55

```
caggtgcagc tggtgcagtc tggggctgag gtgaagaagc ctggggcctc agtgaaggtt      60
tcctgcaagg catctggata caccttcacc aactactata tattctgggt gcgacaggcc     120
cctggacaag ggcttgagtg gatgggagac attaatccta gtaatggtga tactaacttc     180
aatgagaagt tcaagatcag agtcacaatg accagggaca cgtccacgag cacagtctac     240
atggagctga gcagcctgag atctgaggac acggccgtgt attactgtac aagagggggt     300
tatactatgg actactgggg ccaaggaacc ctggtcaccg tctcctca               348
```

<210> SEQ ID NO 56
<211> LENGTH: 116
<212> TYPE: PRT
<213> ORGANISM: Artificial Sequence
<220> FEATURE:
<223> OTHER INFORMATION: Humanized Clone 3 Heavy (B)

<400> SEQUENCE: 56

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Tyr Ile Phe Trp Val Arg Gln Ala Pro Gly Gln Gly Leu Glu Trp Met
        35                  40                  45

Gly Asp Ile Asn Pro Ser Asn Gly Asp Thr Asn Phe Asn Glu Lys Phe
    50                  55                  60

Lys Ile Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Thr Met Asp Tyr Trp Gly Gln Gly Thr Leu Val
            100                 105                 110

Thr Val Ser Ser
        115
```

<210> SEQ ID NO 57
<211> LENGTH: 336
<212> TYPE: DNA
<213> ORGANISM: Artificial Sequence
<220> FEATURE:
<223> OTHER INFORMATION: Humanized Clone 3 Light (C)

<400> SEQUENCE: 57

```
gatgttgtga tgacccagac tccactctct ctgtccgtca cccctggaca gccggcctcc      60
atctcctgca gatctagtca gagccttgta cacagtaatg gaaacaccta ttttcattgg     120
tacctgcaga agccaggcca gcctccaaaa ctcctgatct ataaagtttc ctaccgattt     180
tctggagtgc cagataggtt cagtggcagc gggtcaggga cagatttcac actgaaaatc     240
agccgggtgg aggctgagga tgttggggtt tatttctgct ctcaaagtac acatgttcct     300
cggacgttcg gccaagggac caaggtggaa atcaaa                               336
```

<210> SEQ ID NO 58
<211> LENGTH: 112
<212> TYPE: PRT
<213> ORGANISM: Artificial Sequence
<220> FEATURE:
<223> OTHER INFORMATION: Humanized Clone 3 Light (C)

<400> SEQUENCE: 58

```
Asp Val Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
            20                  25                  30

Asn Gly Asn Thr Tyr Phe His Trp Tyr Leu Gln Lys Pro Gly Gln Pro
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Phe Cys Ser Gln Ser
            85                  90                  95

Thr His Val Pro Arg Thr Phe Gly Gln Gly Thr Lys Val Glu Ile Lys
            100                 105                 110

<210> SEQ ID NO 59
<211> LENGTH: 336
<212> TYPE: DNA
<213> ORGANISM: Artificial Sequence
<220> FEATURE:
<223> OTHER INFORMATION: Humanized Clone 3 Light (D)

<400> SEQUENCE: 59
gatattgtga tgacccagac tccactctct ctgtccgtca cccctggaca gccggcctcc     60
atctcctgca gatctagtca gagccttgta cacagtaatg aaacaccta ttttcattgg    120 tacctgcaga agccaggcca gcctccacag ctcctgatct ataaagtttc ctaccgattt   180
tctggagtgc cagataggtt cagtggcagc gggtcaggga cagatttcac actgaaaatc   240
agccgggtgg aggctgagga tgttggggtt tattactgct ctcaaagtac acatgttcct   300
cggacgttcg gccaagggac caaggtggaa atcaaa                            336

<210> SEQ ID NO 60
<211> LENGTH: 112
<212> TYPE: PRT
<213> ORGANISM: Artificial Sequence
<220> FEATURE:
<223> OTHER INFORMATION: Humanized Clone 3 Light (D)

<400> SEQUENCE: 60

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Phe His Trp Tyr Leu Gln Lys Pro Gly Gln Pro
        35                  40                  45

Pro Gln Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Arg Thr Phe Gly Gln Gly Thr Lys Val Glu Ile Lys
            100                 105                 110

<210> SEQ ID NO 61
<211> LENGTH: 5
<212> TYPE: PRT
<213> ORGANISM: Artificial Sequence
<220> FEATURE:
<223> OTHER INFORMATION: Clone 3 heavy chain CDR

<400> SEQUENCE: 61

Asn Tyr Tyr Ile Phe
1               5

<210> SEQ ID NO 62
<211> LENGTH: 17
<212> TYPE: PRT
<213> ORGANISM: Artificial Sequence
<220> FEATURE:
<223> OTHER INFORMATION: Clone 3 heavy chain CDR

```
<400> SEQUENCE: 62

Asp Ile Asn Pro Ser Asn Gly Asp Thr Asn Phe Asn Glu Lys Phe Lys
1               5                   10                  15

Ile

<210> SEQ ID NO 63
<211> LENGTH: 7
<212> TYPE: PRT
<213> ORGANISM: Artificial Sequence
<220> FEATURE:
<223> OTHER INFORMATION: Clone 3 heavy chain CDR

<400> SEQUENCE: 63

Gly Gly Tyr Thr Met Asp Tyr
1               5

<210> SEQ ID NO 64
<211> LENGTH: 16
<212> TYPE: PRT
<213> ORGANISM: Artificial Sequence
<220> FEATURE:
<223> OTHER INFORMATION: Clone 3 light chain CDR

<400> SEQUENCE: 64

Arg Ser Ser Gln Ser Leu Val His Ser Asn Gly Asn Thr Tyr Phe His
1               5                   10                  15

<210> SEQ ID NO 65
<211> LENGTH: 7
<212> TYPE: PRT
<213> ORGANISM: Artificial Sequence
<220> FEATURE:
<223> OTHER INFORMATION: Clone 3 light chain CDR

<400> SEQUENCE: 65

Lys Val Ser Tyr Arg Phe Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Clone 3 light chain CDR

<400> SEQUENCE: 66

Ser Gln Ser Thr His Val Pro Arg Thr
1               5

<210> SEQ ID NO 67
<211> LENGTH: 5
<212> TYPE: PRT
<213> ORGANISM: Artificial Sequence
<220> FEATURE:
<223> OTHER INFORMATION: Humanized Clone 3 heavy chain CDR (A)

<400> SEQUENCE: 67

Asn Tyr Tyr Ile Phe
1               5

<210> SEQ ID NO 68
<211> LENGTH: 17
<212> TYPE: PRT
<213> ORGANISM: Artificial Sequence
<220> FEATURE:
<223> OTHER INFORMATION: Humanized Clone 3 heavy chain CDR (A)
```

```
<400> SEQUENCE: 68

Asp Ile Asn Pro Ser Asn Gly Asp Thr Asn Phe Asn Glu Lys Phe Lys
1               5                   10                  15
Ile

<210> SEQ ID NO 69
<211> LENGTH: 7
<212> TYPE: PRT
<213> ORGANISM: Artificial Sequence
<220> FEATURE:
<223> OTHER INFORMATION: Humanized Clone 3 heavy chain CDR (A)

<400> SEQUENCE: 69

Gly Gly Tyr Thr Met Asp Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: Humanized Clone 3 heavy chain CDR (B)

<400> SEQUENCE: 70

Asn Tyr Tyr Ile Phe
1               5

<210> SEQ ID NO 71
<211> LENGTH: 17
<212> TYPE: PRT
<213> ORGANISM: Artificial Sequence
<220> FEATURE:
<223> OTHER INFORMATION: Humanized Clone 3 heavy chain CDR (B)

<400> SEQUENCE: 71

Asp Ile Asn Pro Ser Asn Gly Asp Thr Asn Phe Asn Glu Lys Phe Lys
1               5                   10                  15
Ile

<210> SEQ ID NO 72
<211> LENGTH: 7
<212> TYPE: PRT
<213> ORGANISM: Artificial Sequence
<220> FEATURE:
<223> OTHER INFORMATION: Humanized Clone 3 heavy chain CDR (B)

<400> SEQUENCE: 72

Gly Gly Tyr Thr Met Asp Tyr
1               5

<210> SEQ ID NO 73
<211> LENGTH: 16
<212> TYPE: PRT
<213> ORGANISM: Artificial Sequence
<220> FEATURE:
<223> OTHER INFORMATION: Humanized Clone 3 light chain CDR (C)

<400> SEQUENCE: 73

Arg Ser Ser Gln Ser Leu Val His Ser Asn Gly Asn Thr Tyr Phe His
1               5                   10                  15

<210> SEQ ID NO 74
<211> LENGTH: 7
<212> TYPE: PRT
<213> ORGANISM: Artificial Sequence
```

```
<220> FEATURE:
<223> OTHER INFORMATION: Humanized Clone 3 light chain CDR (C)

<400> SEQUENCE: 74

Lys Val Ser Tyr Arg Phe Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Humanized Clone 3 light chain CDR (C)

<400> SEQUENCE: 75

Ser Gln Ser Thr His Val Pro Arg Thr
1               5

<210> SEQ ID NO 76
<211> LENGTH: 16
<212> TYPE: PRT
<213> ORGANISM: Artificial Sequence
<220> FEATURE:
<223> OTHER INFORMATION: Humanized Clone 3 light chain CDR (D)

<400> SEQUENCE: 76

Arg Ser Ser Gln Ser Leu Val His Ser Asn Gly Asn Thr Tyr Phe His
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: Humanized Clone 3 light chain CDR (D)

<400> SEQUENCE: 77

Lys Val Ser Tyr Arg Phe Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Humanized Clone 3 light chain CDR (D)

<400> SEQUENCE: 78

Ser Gln Ser Thr His Val Pro Arg Thr
1               5
```